United States Patent [19]

Taylor, Jr. et al.

[11] Patent Number: 4,826,866
[45] Date of Patent: May 2, 1989

[54] 3-AMINO-5-METHYL-1H-PYRAZOLE-4-CARBOXYLIC ACIDS AND ESTERS THEREOF AS ANTICONVULSANTS, MUSCLE RELAXANTS AND ANXIOLYTICS

[75] Inventors: Chandler R. Taylor, Jr., Mechanicsville; Harold F. Stauffer, Jr., Midlothian, both of Va.

[73] Assignee: A. H. Robins Company, Incorporated, Richmond, Va.

[21] Appl. No.: 115,918

[22] Filed: Nov. 2, 1987

[51] Int. Cl.$^4$ .................................. A61K 31/415
[52] U.S. Cl. .................................. 514/403
[58] Field of Search .................................. 514/403

Primary Examiner—Stanley J. Friedman

[57] ABSTRACT

A novel method of controlling epilepsy, muscle tension, muscular spasticity, and anxiety in living animal bodies by administering compounds of the formula:

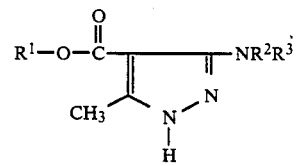

wherein:
$R^1$ is hydrogen, loweralkyl or a pharmaceutically acceptable cation;
$R^2$ and $R^3$, same or different, are hydrogen, loweralkyl, aryl, cycloalkyl, loweralkenyl, 1-adamantyl, heterocyclicaminoalkyl, diloweralkylaminoloweralkyl, or $R^2$ with $R^3$ and adjacent nitrogen may form a heterocyclic ring structure; and the pharmaceutical acceptable acid salts, and tautomeric isomers thereof; and novel pharmaceutical compositions therefor are disclosed.

66 Claims, No Drawings

3-AMINO-5-METHYL-1H-PYRAZOLE-4-CARBOXYLIC ACIDS AND ESTERS THEREOF AS ANTICONVULSANTS, MUSCLE RELAXANTS AND ANXIOLYTICS

BACKGROUND OF THE INVENTION

1. Field of Invention

The present invention relates to a novel method of controlling epilepsy, muscle tension, muscular spasticity, and anxiety in living mammal bodies which utilizes certain 3-amino-5-methyl-1H-pyrazole-4-carboxylic acids and esters; and novel pharmaceutical compositions therefor are disclosed.

2. Information Disclosure Statement

3-Amino-5-substituted-1H-pyrazole-4-carboxylic acids identical or similar to those useful in the novel methods of the present invention have been disclosed as herbicides in German Offen. No. 2,747,531.

5-Amino-1,3-substituted-4-pyrazolecarboxanilides having anticonvulsant activity are disclosed in U.S. Pat. No. 4,346,097 and in U.S. Pat. No. 4,393,217 as having anxiolytic and antidepressant activity. In contrast compounds of the present invention are 4-carboxylates and 4-carboxylic acids.

3-Anilido-5-substituted-1H-pyrazole-4-carboxylic acid esters have been disclosed in Japan Kokai No. 74 95,968 to be an effective remedy against smallpox virus.

OBJECTIVES AND SUMMARY OF THE INVENTION

The present invention is concerned with a novel method of treating epilepsy, muscle tension, muscle spasticity, and anxiety in a living mammal which comprises administering to a mammal in need thereof a 3-amino-5-methyl-1H-pyrazole-4-carboxylic acid or an ester thereof having the following formula:

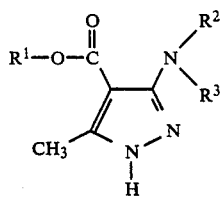

Formula I wherein:
$R^1$ is hydrogen, loweralkyl or a pharmaceutically acceptable cation;
$R^2$ and $R^3$, same or different, are hydrogen, loweralkyl, aryl, cycloalkyl, loweralkenyl, 1-adamantyl, heterocyclicaminoalkyl, diloweralkylaminoloweralkyl or $R^2$ with $R^3$ and adjacent nitrogen forming the heterocyclic ring structure 4-morpholino, 4-substituted-1-piperazinyl, 1-piperazinyl, 1-piperidinyl, 1-pyrrolidinyl, or 1-homopiperidinyl;
and the pharmaceutically acceptable salts thereof; and the tautomeric isomers thereof.

In further definition of the symbols in Formula I and where they appear elsewhere throughout this specification and claims, the terms have the following significance:

The term "loweralkyl" as used herein includes straight and branched chain radicals up to eight carbons inclusive and is exemplified by such groups as methyl, ethyl, propyl, isopropyl, butyl, sec.butyl, tert.butyl 1,1,3,3-tetramethylbutyl, amyl, isoamyl, hexyl, heptyl, and octyl radicals and the like. The term "loweralkoxy" as used herein has the formula —O-loweralkyl.

The term "aryl" as used herein includes pyridinyl in any of its positions, naphthalenyl in any of its positions, phenyl and phenyl-loweralkyl wherein phenyl may be substituted by one to three radicals, same or different, and are halogen, methylthio, loweralkyl, loweralkoxy, or trifluoromethyl.

The term "pharmaceutically acceptable cation" as used herein refers primarily to a pharmaceutically acceptable metal such as sodium, potassium, magnesium, zinc, copper, aluminum and the like.

The term "cycloalkyl" includes primarily cyclic and polycyclic alkyl radicals of three to ten carbon atoms and includes such groups as cyclopropyl, cyclobutyl, cyclopentyl, cyclohexyl, cycloheptyl, cyclooctyl, 1-adamantyl and the like.

The term "loweralkenyl" as used herein refers to a loweralkyl radical containing a carbon-carbon double bond.

The term "heterocyclicaminoalkyl" as used herein refers primarily to a heterocyclic amino radical having 5-7 ring members and exemplified by such groups as 4-morpholinyl, 1-pyrrolidinyl, 1-piperidinyl, 4-substituted-1-piperazinyl, 1-piperazinyl, 1-homopiperidinyl and the like, connected via a 1-8 carbon alkyl chain, including branched chains, to a nitrogen of the heterocyclic amino ring.

The term "heterocyclic ring structure" as used herein includes primarily the heterocyclic amino radicals 1-azetidinyl, 1-pyrrolidinyl, 1-piperidinyl, 1-homopiperidinyl, 1-piperizinyl and the like.

The term "4-substituted-1-piperazinyl" as used herein refers to a piperazine radical substituted by usual groups common in the pharmaceutical art including "aryl" and "loweralkyl" as defined above.

The term "pharmaceutically acceptable salts" as used herein refers to those acid addition salts, quarternary salts, carboxylic acid salts, alcoholates and hydrates that are physiologically compatible in mammals. The acid addition salts may be formed by either strong or weak acids. Representative of useful strong acids are hydrochloride, hydrobromic, sulfuric, phosphoric and the like. Representative of useful weak acids are fumaric, maleic, succinic, oxalic, citric, tartaric, hexamic and the like. Suitable quarternary salts include loweralkyl halides and sulfates. Suitable carboxylic acid salts are formed by such as the alkali metals, alkaline earth metals, copper, aluminum and the like.

The term "tautomeric isomers" refers to the possible existence of the compounds of Formula I, in two forms, Ia and Ib. as follows:

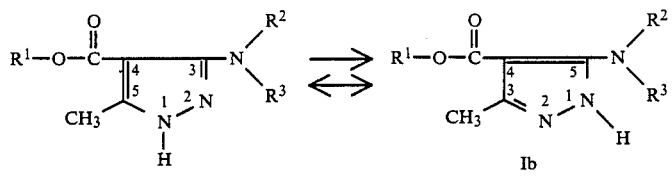

and it is understood the compounds may exist in one or both tautomeric forms depending on such factors as the various substituents which make up the molecule, and when in solution, on the nature of the solvent. For purposes of simplicity, the numbering system used herein corresponds to that of Formula Ia.

The compounds of Formula I of this invention are useful because of their pharmacological action on the central nervous system. This method employs the compounds of Formula I to treat a living mammal (e.g., humans) for muscle tension and spasticity (i.e., to relax muscles), to control anxiety and to treat epilepsy (control convulsions).

The procedure used for testing compounds for their muscle relaxant activity is the Morphine-Induced-Straub-Tail-Test. The procedure used for testing compounds for their anticonvulsant activity is based on evaluation of protective activity against seizures induced by electrical or chemical challenge. The procedure used for testing compounds for antianxiety activity is the Vogel Conflict Test, which is based on the shock-suppressed drinking behavior of rats. All of these evaluation techniques are described in greater detail under Pharmacological Test Procedures, hereinbelow.

It is therefore an object of the present invention to provide certain 3-amino-5-methyl-1H-pyrazole-4-carboxylic acids and acid esters thereof, as described hereinabove and as defined under Formula I which has CNS activity in a novel method of treatment for epilepsy, muscle tension, spastic muscles, and anxiety.

Additional objects and advantages of the present invention will be apparent to one skilled in the art and others will become apparent from the following description of the best mode of carrying out the invention, and from the appended claims.

DETAILED DESCRIPTION OF THE INVENTION

The novel methods of treating epilepsy, anxiety, muscle tension, and muscle spasticity in living animals comprises administering a 3-amino-5-methyl-1H-pyrazole-4-carboxylic acid or carboxylic acid ester and derivatives thereof as set forth hereinabove under Formula I and in definitions therewith, and as pharmaceutical compositions to a living animal body for anticonvulsant, muscle relaxant, or antianxiety effect in an effective amount.

The compounds of Formula I are prepared by one of three methods as outlined hereinbelow under methods A, B, and C.

Method A. This method is represented by the following equation:

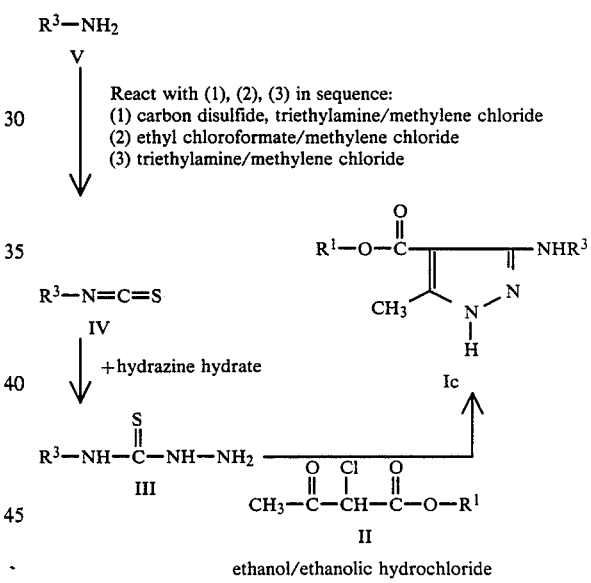

wherein:
$R^1$ and $R^3$ are as defined hereinabove under Formula I.

Generally in Method A, a primary amine of Formula V is reacted first with carbon disulfide and triethylamine in solvent, e.g., methylene chloride and treated with ethyl chloroformate and triethylamine in appropriate solvents in a procedure similar to that used by Garmaise et al., J. Amer. Chem. Soc. 80: 3332 (1958), giving an isothiocyanate product of Formula IV. This product is reacted with hydrazine hydrate as in the method of Pohloudek, Fabini and Göckeritz, Pharmazie, 17, No. 9, 515 (1962) to give a thiosemicarbazide of Formula III, which is reacted with a compound of Formula II as in the method of Bulka et al., Chem. Ber. 98, 259 (1965) to give a compound of Formula Ic. Pharmaceutically acceptable acid addition salts may be prepared by reacting the free base with the appropriate acid.

Method B. This method is represented by the following equations:

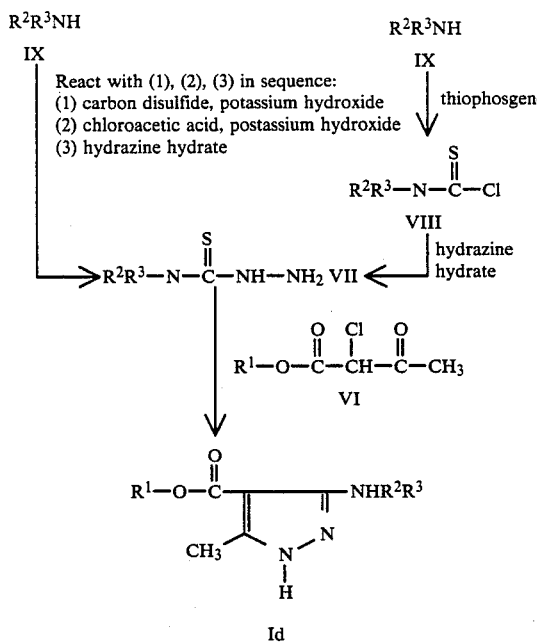

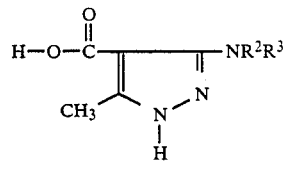

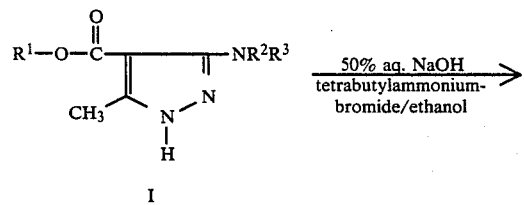

wherein:

$R^1$, $R^2$, and $R^3$ are as defined hereinabove under Formula I, except that when a Formula IX compound is reacted with thiophosgene $R^2$ and $R^3$ are not hydrogen, and $R^2$ with $R^3$ and adjacent nitrogen do not form the heterocyclic ring structure 1-piperazinyl in this method, but may form the heterocyclic ring structure 4-substituted-1-piperazinyl.

Generally in Method B, an amine of Formula IX is reacted in sequence with carbon disulfide, chloroacetic acid, and hydrazine hydrate, as in the method of Jensen, K. A. J. Prakt. Chem. 159, 189 (194) to give a thiosemicarbazide of Formula VII. Optionally, a secondary amine of Formula IX may be reacted with thiophosgene to give a compound of Formula VIII, followed by reaction with hydrazine hydrate to give the desired thiosemicarbazide of Formula VII as in the method of Jensen, et al., Acta. Chem. Scand. 22, 37 (1968). In any event, reaction of the obtained thiosemicarbazide with a compound of Formula VI, by the method of Bulka, et al., Chem. Ber. 98, 259 (1965) gives a compound of Formula Id. Pharmaceutically acceptable salts may be prepared by reacting the free base with the appropriate acid.

Method C. This method is represented by the following equation:

wherein:

$R^1$, $R^2$, and $R^3$ are as defined hereinabove under Formula I, except $R^1$ is not hydrogen in this method.

Generally in Method C, a carboxylic acid ester of Formula I is hydrolyzed by use of a phase transfer catalyst such as tetrabutylammonium bromide in a suitable solvent such as ethyl alcohol. The reaction mixture is stirred at ambient temperature for about 24 hr, diluted with water, and extracted with an appropriate organic solvent such as isopropyl ether. Acidification of the extracted organic layer to about approximately pH 6 precipitates the desired compound of Formula Ie, which may then be purified and/or dried by the usual means known in the art. The method is illustrated more fully in Example 45. Pharmaceutically acceptable acid addition salts may be prepared by reacting with the appropriate acid.

Many of the starting compounds used in the novel methods of the present invention, i.e., starting amine compounds, compounds of Formula V and Formula IX are available commercially through Aldrich Chemical Co., Inc., 940 West Saint Paul Avenue, Milwaukee, WI 53233. Other starting compounds useful in the methods of the present invention are readily prepared by known methods of chemical synthesis used in the art, or are obvious variations thereof. The following preparations and examples serve to illustrate methods of preparing the compounds useful in the novel methods of the present invention. The scope of the invention is not limited by the Preparations and Examples, however. Structures of the compounds of the Examples are given for reference in Table I.

Preparation 1

Utilizing Method A and the procedure of Garmaise, et al., J. Amer. Chem. Soc., 80, 3332 (1958), and the procedure of Pohloudek-Fabrini and Göckeritz, Pharmazie, 17, No. 9, 515 (1962) and reacting the following:
(a) aniline,
(b) 4-chloroaniline,
(c) 3-(methylmercapto)aniline,
(d) 1-aminonaphthalene,
(e) 2-(methylmercapto)aniline,
(f) 2,6-dimethylaniline,
(g) 2-methoxyaniline,
(h) o-toluidine,
(i) 2,6-dichloroaniline,
(j) 2-chloroaniline,
(k) 2,4-dimethoxyaniline,
(l) 3-chloroaniline,
(m) 2-aminopyridine,
(n) butylamine,
(o) 2,6-diethylaniline,
(p) 2,4-dimethylaniline,
(q) 4-chloro-2-methylaniline,
(r) 2,4-dichloroaniline,
(s) 2-chloro-6-methylaniline, (t) 4-bromo-2,6-dimethylaniline,
(u) methylamine,
(v) allylamine,
(w) ethylamine,
(x) cyclohexylamine,
(y) benzylamine, and
(z) 1-adamantanamine
in sequence with
(1) carbon disulfide and triethylamine, solvent (e.g. methylene chloride)
(2) ethyl chloroformate/methylene chloride, and
(3) triethylamine/methylene chloride followed by hydrazine hydrate,
there are obtained:
(a) 4-phenyl-3-thiosemicarbazide,
(b) 4-(4-chlorophenyl)-3-thiosemicarbazide,
(c) 4-[3-(methylthio)phenyl]-3-thiosemicarbazide,
(d) 4-(1-naphthalenyl)-3-thiosemicarbazide,
(e) 4-[2-(methylthio)phenyl]-3-thiosemicarbazide,
(f) 4-(2,6-dimethylphenyl)-3-thiosemicarbazide,
(g) 4-(2-methoxyphenyl)-3-thiosemicarbazide,
(h) 4-(2-methylphenyl)-3-thiosemicarbazide,
(i) 4-(2,6-dichlorophenyl)-3-thiosemicarbazide,
(j) 4-(2-chlorophenyl)-3-thiosemicarbazide,
(k) 4-(2,4-dimethoxyphenyl)-3-thiosemicarbazide,
(l) 4-(3-chlorophenyl)-3-thiosemicarbazide,
(m) 4-(2-pyridyl)-3-thiosemicarbazide,
(n) 4-butyl-3-thiosemicarbazide,
(o) 4-(2,6-diethylphenyl)-3-thiosemicarbazide,
(p) 4-(2,4-dimethylphenyl)-3-thiosemicarbazide,
(q) 4-(4-chloro-2-methylphenyl)-3-thiosemicarbazide,
(r) 4-(2,4-dichlorophenyl)-3-thiosemicarbazide,
(s) 4-(2-chloro-6-methylphenyl)-3-thiosemicarbazide,
(t) 4-(4-bromo-2,6-dimethylphenyl)-3-thiosemicarbazide,
(u) 4-methyl-3-thiosemicarbazide,
(v) 4-(2-propenyl)-3-thiosemicarbazide,
(w) 4-ethyl-3-thiosemicarbazide,
(x) 4-cyclohexyl-3-thiosemicarbazide,
(y) 4-phenylmethyl-3-thiosemicarbazide, and
(z) 4-(1-adamantyl)-3-thiosemicarbazide.

Preparation 2

Utilizing Method A and the procedure of Garmaise, et al., J. Amer. Chem. Soc., 80, 3332 (1958) and the procedure of Pohloudek-Fabrini and Göckeritz, Pharmazie, 17, No. 9, 515 (1962) and reacting the following:
(a) phenethylamine,
(b) heptylamine,
(c) tert-butylamine,
(d) cycloheptylamine,
(e) cyclopentylamine,
(f) cyclopropylamine,
(g) propylamine,
(h) sec-butylamine,
(i) amylamine,
(j) hexylamine,
(k) cyclooctylamine,
(l) 2-methylbutylamine,
(m) tert-octylamine,
(n) 3-dimethylaminopropylamine,
(o) 1-(2-aminoethyl)piperidine,
(p) isopropylamine,
(q) 4-(2-aminoethyl)morpholine,
(r) 4-(3-aminopropyl)morpholine, and
(s) 4-aminobenzotrifluoride
in sequence with
(1) carbon disulfide and triethylamine, solvent (e.g. methylene chloride)
(2) ethyl chloroformate/methylene chloride, and
(3) triethylamine/methylene chloride followed by hydrazine hydrate,
there are obtained:
(a) 4-phenylethyl-3-thiosemicarbazide,
(b) 4-heptyl-3-thiosemicarbazide,
(c) 4-(1,1-dimethylethyl)-3-thiosemicarbazide,
(d) 4-cycloheptyl-3-thiosemicarbazide,
(e) 4-cyclopentyl-3-thiosemicarbazide,
(f) 4-cyclopropyl-3-thiosemicarbazide,
(g) 4-propyl-3-thiosemicarbazide,
(h) 4-(2-butyl)-3-thiosemicarbazide,
(i) 4-pentyl-3-thiosemicarbazide,
(j) 4-hexyl-3-thiosemicarbazide,
(k) 4-cyclooctyl-3-thiosemicarbazide,
(l) 4-(2-methylbutyl)-3-thiosemicarbazide,
(m) 4-(1,1,3,3-tetramethylbutyl)-3-thiosemicarbazide,
(n) 4-(3-dimethylaminopropyl)-3-thiosemicarbazide,
(o) 4-(2-(1-piperidinyl)ethyl)-3-thiosemicarbazide,
(p) 4-(1-methylethyl)-3-thiosemicarbazide,
(q) 4-[2-(4-morpholinyl)ethyl]-3-thiosemicarbazide,
(r) 4-[3-(4-morpholinyl)propyl]-3-thiosemicarbazide, and
(s) 4-[4-(trifluoromethyl)phenyl]-3-thiosemicarbazide.

Preparation 3

Utilizing Method B and the procedure of Jensen, et al., Acta Chem. Scand., 22, 37 (1968) and reacting the following:
(a) dimethylamine,
(b) di-n-butylamine,
(c) morpholine,
(d) N-methylcyclohexylamine,
(e) N-methylcyclopentylamine,
(f) 1-phenylpiperazine,
(g) 1-benzylpiperazine,
(h) pyrrolidine,
(i) piperidine, and
(j) homopiperidine
with thiophosgene followed by hydrazine hydrate, there are obtained:
(a) 4,4-dimethyl-3-thiosemicarbazide,
(b) 4,4-dibutyl-3-thiosemicarbazide,
(c) 4-morpholinecarbothioic acid hydrazide,
(d) 4-cyclohexyl-4-methyl-3-thiosemicarbazide,
(e) 4-cyclopentyl-4-methyl-3-thiosemicarbazide,
(f) (4-phenyl-1-piperazine)carbothioic acid hydrazide,
(g) (4-phenylmethyl-1-piperazine)carbothioic acid hydrazide,
(h) 1-pyrrolidinecarbothioic acid hydrazide,
(i) 1-piperidinecarbothioic acid hydrazide, and
(j) 1-homopiperidinecarbothioic acid hydrazide.

EXAMPLE 1

5-Methyl-3-phenylamino-1H-pyrazole-4-carboxylic acid, ethyl ester

A suspension of 16.7 g (0.1 mole) of 4-phenyl-3-thiosemicarbazide in 60 mL of absolute ethanol was treated with 16.5 g (0.1 mole) of ethyl 2-chloroacetoacetate and the mixture stirred for 1 hr at room temperature. As the thiosemicarbazide began to dissolve the reaction mixture became exothermic and a reddish-brown solid precipitated. Alcoholic hydrogen chloride (2N, 50 mL) was added, and the reaction mixture heated at reflux for 1.0 hr. The solution was filtered while hot and the filtrate was evaporated under reduced pressure. The solid residue was triturated in cold absolute ethanol and a red solid collected by filtration. The solid was warmed in 2N hydrochloric acid (100 mL) and the suspended sulfur removed by filtration. An orange-red solid precipitated from the filtrate, was collected by filtration and air dried for ~16 hr (14.6 g, mp 160°–40° C.). Recrystallization from benzene left 10.5 g of product, mp 165°–6° C. The material was air dried and submitted for elemental analysis.

Analysis: Calculated for $C_{13}H_{15}N_3O_2$: C, 63.66; H, 6.16; N, 17.13; Found: C, 63.63; H, 6.22; N, 17.13.

EXAMPLE 2

3-[(4-Chlorophenyl)amino]-5-methyl-1H-pyrazole-4-carboxylic acid, ethyl ester

A suspension of 20.1 g (0.10 mole) of 4-(4-chlorophenyl)-3-thiosemicarbazide in 80 mL of absolute ethanol was treated with 16.5 g (0.10 mole) of ethyl 2-chloroacetoacetate and the mixture stirred for 1.0 hr at room temperature. Alcoholic hydrogen chloride (2N, 60 mL) was added and the dark precipitate dissolved while heating the mixture at reflux for 1.0 hr. The solution was filtered while hot, and the filter cake washed with absolute ethanol. The filtrate was evaporated under reduced pressure and the residue triturated in cold absolute ethanol and filtered. Both filter cakes were found to be the same compound by TLC (10% methanol in benzene on silica gel). The two were combined, dissolved in hot absolute ethanol (the hydrochloride salt was water insoluble), partially neutralized with saturated aqueous sodium bicarbonate, and the solid filtered (10.4 g, mp 212°–226° C.). A second crop was obtained by treating the filtrate with saturated aqueous sodium bicarbonate (11.5 g, mp 220°–225° C.). The second crop was recrystallized from absolute ethanol to give 3.8 g of product, mp 223°–225° C. This solid was dried at 100° C./0.1 mmHg/3 hr; then for ~16 hr at RT/0.1 mmHg.

Analysis: Calculated for $C_{13}H_{14}ClN_3O_2$: C, 55.82; H, 5.05; N, 15.02; Found: C, 55.85; H, 5.08; N, 15.10.

EXAMPLE 3

5-Methyl-3-[[3-(methylthio)phenyl]amino]-1H-pyrazole-4-carboxylic acid, ethyl ester A suspension of 10.0 g (0.046 mole) of 4-(3-methylthiophenyl)-3-thiosemicarbazide and 7.72 g (0.0469 mole) of ethyl 2-chloroacetoacetate in 150 mL of absolute ethanol was stirred at room temperature for ~16 hr. Ethanolic hydrogen chloride (2N, 50 mL) was added, the mixture refluxed for 1.0 hr, the solution filtered while hot, and the filtrate evaporated under reduced pressure to give a crystalline residue which was recrystallized three times from absolute ethanol to give 6.3 g product, mp 191.5°–194° C. The sample was dried at 56° C./4 hr/0.1 mmHg then 2 hr/25° C./0.1 mmHg.

Analysis: Calculated for $C_{14}H_{17}N_3O_2S$: C, 57.71; H, 5.88; N, 14.42; Found: C, 57.97; H, 5.94; N, 14.58.

EXAMPLE 4

5-Methyl-3-(1-naphthalenylamino)-1H-pyrazole-4-carboxylic acid, ethyl ester

A suspension of 15.0 g (0.069 mole) of 4-(1-naphthalenyl)-3-thiosemicarbazide and 11.4 g (0.069 mole) of ethyl 2-chloroacetoacetate in 100 mL of absolute ethanol was stirred at room temperature for 1 hr. Alcoholic hydrogen chloride (2N, 50 mL) was added, the mixture refluxed for 1 hr, filtered while hot and the filtrate evaporated under reduced pressure. The residue was recrystallized twice from 190 ethanol then twice from absolute ethanol to give 6.2 g of product, mp 199°–202° C. The sample was dried at 56° C./4 hr/0.1 mmHg then at 25° C./0.1 mmHg/for ~16 hr.

Analysis: Calculated for $C_{17}H_{17}N_3O_2$: C, 69.14; H, 5.80; N, 14.23; Found: C, 69.05; H, 5.86; N, 14.23.

EXAMPLE 5

5-Methyl-3-[[2-(methylthio)phenyl]amino]-1H-pyrazole-4-carboxylic acid, ethyl ester A mixture of 15 g (0.07 mole) of 4-[2-(methylthio)phenyl]-3-thiosemicarbazide and 11.96 g (0.07 mole) of ethyl 2-chloroacetoacetate (97%) in 100 mL of absolute ethanol was stirred under nitrogen atmosphere for 1 hr at room temperature. The reaction was slightly exothermic and the mixture took on a yellow color as most of the solid dissolved. The mixture was treated with 50 mL of 2N ethanolic hydrogen chloride and heated at reflux for 1.5 hr. The mixture had darkened to a deep, clear, orange color, with only a trace of insoluble material which was removed by filtering through a sintered glass filter. The solvent was removed in vacuo giving a yellow-orange solid (18.6 g). The solid was recrystallized from acetone, 17.4 g (85% yield), mp 135°–158° C. Thin layer chromatography indicated two impurities (10% methanol/benzene on silica gel). This crude product was recrystallized from benzene/ligroin to give 12.1 g (59% yield), mp 126°–128° C. (some solid remained and melted at 158°–160° C.). Thin layer chromatography indicated that one of the two impurities had been removed. The solid was dissolved in methylene chloride and chromatographed on a 250 g column of Florisil ® (60–100 mesh). The column was eluted with methylene chloride. The solid obtained was recrystallized from benzene-ligroin giving 4.6 g (22.5%) of product, mp 140.5°–142° C.

Analysis: Calculated for $C_{14}H_{17}N_3O_2S$: C, 57.71; H, 5.88; N, 14.42; Found: C, 57.87; H, 5.89; N, 14.35.

EXAMPLE 6

5-Methyl-3-[(2,6-dimethylphenyl)amino]-1H-pyrazole-4-carboxylic acid, ethyl ester A mixture of 9.8 g (0.05 mole) of 4-(2,6-dimethylphenyl)-3-thiosemicarbazide and 8.48 g (0.05 mole) of ethyl 2-chloroacetoacetate (97%) in 75 mL of absolute ethanol was stirred under nitrogen atmosphere for one hour at room temperature. The reaction was slightly exothermic and the mixture changed from a white slurry to a yellow slurry as most of the solid dissolved. The mixture was treated with 40 mL of 2N ethanolic hydrogen chloride and allowed to stir at room temperature for 16 hr. The reaction mixture was heated at reflux for two hours; during this time it took on a dark orange color which cleared later as all the material dissolved (a small amount of insoluble material was also present). The reaction mixture was filtered and the solvent removed under reduced pressure leaving a yellow-orange solid. The solid was triturated with acetone which dissolved most of the orange color. Filtration gave 12.6 g of pale yellow crystals, mp 131°–137° C. Recrystallization of the yellow solid from acetone gave two crops of soft, fluffy, white product. Both crops were combined and analyzed, yield 8.5 g (62%), mp 142°–144° C.

Analysis: Calculated for $C_{15}H_{19}N_3O_2$: C, 65.91; H, 7.01; N, 15.37; Found: C, 65.82; H, 6.93; N, 15.37.

EXAMPLE 7

5-Methyl-3-[(2-methoxyphenyl)amino]-1H-pyrazole-4-carboxylic acid, ethyl ester

A suspension of 10.0 g (0.0507 mole) of 4-(2-methoxyphenyl)-3-thiosemicarbazide and 8.35 g (0.0507 mole) of ethyl 2-chloroacetoacetate in 150 mL of absolute ethanol was stirred for ~16 hr at room temperature. Alcoholic hydrogen chloride (2N, 50 mL) was added, the mixture heated at reflux for 1.0 hr, and the solution filtered while hot to remove precipitated sulfur. The filtrate was evaporated under reduced pressure, and the residue dissolved in hot ethanol, treated with charcoal and filtered through Celite®. The solution deposited 10.0 g of product, mp 162°-172° C. A similar recrystallization from absolute ethanol left 8.1 g, mp 155°-175° C. This product was dissolved in absolute ethanol, treated with charcoal, and filtered through Celite® 3 times. The filtrate deposited 4.3 g of product while standing for ~16 hr, mp 155.5°-159° C. which was a mixture of free base and hydrochloride salt. This last filtrate was left open to the atmosphere, and after approximately 50% of the solvent had evaporated, a solid precipitated and was collected by filtration: 1.4 g, mp 184°-191° C.

Analysis: Calculated for $C_{14}H_{17}N_3O_3$: C, 61.08; H, 6.22; N, 15.26; Found: C, 60.98; H, 6.19; N, 15.16.

EXAMPLE 8

5-Methyl-3-[(2-methylphenyl)amino]-1H-pyrazole-4-carboxylic acid, ethyl ester

A stirred slurry of 4-(2-methylphenyl)-3-thiosemicarbazide, 15.3 g (0.08 mole), in 100 mL of absolute ethanol was treated under nitrogen atmosphere with ethyl 2-chloroacetoacetate, 13.61 g (0.08 mole). After stirring for 1 hr the slurry had turned from white to yellow with most of the material going into solution. The reaction mixture was treated with 50 mL of 2N ethanolic hydrogen chloride and stirred for 18 hr., after which the reaction mixture was heated at reflux for 2 hours. A clear orange solution was decanted from some residual material. The hot solution was filtered through a sintered glass filter and the filtrate concentrated in vacuo to give a yellow solid residue. This residue was dissolved in 500 mL of acetone and 50 mL methanol. After filtering, the volume of the filtrate was concentrated to 125 mL under nitrogen atmosphere. The product was allowed to crystallize at ~7°-10° C. for ~72 hr. Some sulfur crystals separated and were removed by filtration. The filtrate was again concentrated in vacuo to a solid. The solid was dissolved in hot acetone and upon cooling at ~7°-10° C., long needle-like crystals formed and redissolved on warming to room temperature. The solution was treated with water and overnight gave pale, yellow needle-like crystals which, after drying, weighed 15 g, mp 156°-160° C. After 3 recrystallizations from benzene/ligroin a fine white crystalline solid was obtained (8.6 g, mp 160°-161° C.).

Analysis: Calculated for $C_{14}H_{17}N_3O_2$: C, 64.85; H, 6.61; N, 16.21; Found: C, 64.88; H, 6.59; N, 16.33.

EXAMPLE 9

3-[(2,6-Dichlorophenyl)amino]-5-methyl-1H-pyrazole-4-carboxylic acid, ethyl ester A slurry of 9.4 g (0.04 mole) of 4-(2,6-dichlorophenyl)-3-thiosemicarbazide in 75 mL of absolute ethanol was stirred under nitrogen atmosphere while 6.8 g (0.04 mole) of ethyl 2-chloroacetoacetate was added. The reaction mixture became yellow as it stirred for 1 hr at room temperature. Then 40 mL of 2N ethanolic hydrogen chloride was added and the reaction mixture heated at reflux for 3 hr. Insoluble sulfur was removed by filtration and the filtrate concentrated in vacuo to give an orange solid, which when triturated with hot acetone yielded 11.3 g of pale yellow crystals, mp: plastic 175°-191° C., degasses at 195° C. and forms a clear melt at 215° C. Recrystallization from acetonitrile gave 6.5 g of product, mp 180°-190° C. Additional material was obtained from the reaction mixture filtrate upon setting. The filtrate was then concentrated to a solid. All crude materials were combined and dissolved in 125 mL of benzene, treated with charcoal, filtered, and the volume reduced to 40 mL. The benzene solution was treated with 25 mL of ligroin and the product crystallized from the hot solution to give 9.7 g of crystalline product which had a pink color, mp 191°-192° C.

Analysis: Calculated for $C_{13}H_{13}N_3O_2Cl_2$: C, 49.70; H, 4.17; N, 13.38; Found: C, 49.50; H, 4.21; N, 13.26.

EXAMPLE 10

3-[2-Chlorophenyl)amino]-5-methyl-1H-pyrazole-4-carboxylic acid, ethyl ester

A solution of 10.05 g (0.05 mole) of 4-(2-chlorophenyl)-3-thiosemicarbazide in 75 mL of absolute ethanol was treated with 8.48 g (0.05 mole) of ethyl 2-chloroacetoacetate and stirred under nitrogen atmosphere at room temperature for 1 hr. The reaction mixture was treated with 40 mL of 2N ethanolic hydrogen chloride and heated at reflux for 1 hr, during which time the yellow slurry became a clear, deep orange solution. The characteristic insoluble amorphous sulfur was removed by filtration. The filtrate began to solidify. It was allowed to cool for approximately 16 hr to yield 10.1 g of yellow crystalline product. The filtrate was concentrated in vacuo to yield an additional 3 g of yellow product. The 2 solids were combined and recrystallized from benzene to give 10.4 g of white crystalline product, mp 188°-189° 1 C.

Analysis: Calculated for $C_{13}H_{14}N_3O_2Cl$: C, 55.82; H, 5.05; N, 15.02; Found: C, 55.45; H, 5.01; N, 14.98.

EXAMPLE 11

3-[(2,4-Dimethoxyphenyl)amino]-5-methyl-1H-pyrazole-4-carboxylic acid, ethyl ester, hydrochloride [1:1]

A stirred slurry of 18.2 g (0.08 mole) of 4-(2,4-dimethoxyphenyl)-3-thiosemicarbazide in 120 mL of absolute ethanol was treated with 13.6 g (0.08 mole) of ethyl 2-chloroacetoacetate, and the slightly exothermic reaction was allowed to stir at room temperature for 2 hr. Most of the solid material dissolved and the solution became yellow. The reaction mixture was treated with 40 mL of 2N ethanolic hydrogen chloride and heated at reflux for 1 hr. At this time point, previous reaction mixtures had become clear solutions. The reaction mixture was diluted with an additional 200 mL of absolute ethanol and heated to reflux. The reactants dissolved and the reaction mixture became orange, and amorphous sulfur separated. The reaction mixture was filtered hot. Some products precipitated in the filter while filtering and were washed out with 100 mL of hot absolute ethanol. The combined reaction mixture volume, now 600 mL, was reduced under a stream of nitrogen, and on cooling overnight yielded 23 g of crystalline product with a yellow color. Recrystallization from ethanol gave 18 g of yellow crystalline product but TLC showed the presence of sulfur. The compound was dissolved in 50 mL of methanol and 100 mL of benzene was added. The volume was reduced to 75 mL, and 50 mL of ligroin was added. After 5 days, filtration yielded 11.4 g of white powder with a pink color, mp 199°–200° C. Elemental analysis indicated that it was the hydrochloride salt.

Analysis: Calculated for $C_{15}H_{20}N_3O_4Cl$: C, 52.71; H, 5.90; N, 12.29; Found: C, 52.69; H, 5.86; N, 12.39.

EXAMPLE 12

3-[(3-Chlorophenyl)amino]-5-methyl-1H-pyrazole-4-carboxylic acid, ethyl ester

A stirred slurry of 8 g (0.04 mole) of 4-(3-chlorophenyl)-3-thiosemicarbazide in 75 mL of absolute ethanol was treated with 6.8 g (0.04 mole) of ethyl 2-chloroacetoacetate. The reactants quickly dissolved but a precipitate soon formed. After stirring at room temperature for 2 hr the reaction mixture was treated with 40 mL of 2N ethanolic hydrogen chloride and heated at reflux for 1 hr, then filtered while hot to remove the insoluble sulfur. The filtrate on cooling yielded 3.5 g of yellow solid and an additional 4.7 g was obtained when the filtrate was concentrated in vacuo. Recrystallization from benzene/ligroin gave 4.2 g of pale yellow brown product. Additional ligroin added to the filtrate gave, upon cooling at ~7°–10° C. for ~16 hr, additional crystals but also some oil; this tri-phase mixture was filtered to yield 1.5 g of additional product. Both solids had identical spectra. They were combined and recrystallized twice from benzene/ligroin and finally from benzene by dissolving the solids and reducing the volume until crystallization began. Upon cooling, 3.93 g of beige plate-like crystals were collected, mp 159.5°–160° C.

Analysis: Calculated for $C_{13}H_{14}N_3O_2Cl$: C, 55.82; H, 5.05; N, 15.02; Found: C, 55.86; H, 5.07; N, 15.20.

EXAMPLE 13

5-Methyl-3-[(2-pyridinyl)amino]-1H-pyrazole-4-carboxylic acid, ethyl ester

A stirred slurry of 4.4 g (0.03 mole) of 4-(2-pyridyl)-3-thiosemicarbazide in 50 mL of absolute ethanol was treated with 5.3 g (0.03 mole) of ethyl 2-chloroacetoacetate and after 2 hr at room temperature the solution had become yellow. The reaction mixture was then treated with 25 mL of 2N ethanolic hydrogen chloride and stirred over the weekend at room temperature. The reaction mixture was heated at reflux for 2 hr, filtered hot and the filtrate concentrated in vacuo to give a yellow-orange oil (8.1 g) which failed to crystallize. After 2 weeks no crystalline product was evident. The oil was dissolved in ethanol/water, made basic with sodium bicarbonate solution, and extracted with $3 \times 100$ mL of methylene chloride. The extracts were combined, washed with 20 mL of water, dried over magnesium sulfate, and concentrated in vacuo to a yellow oil which solidified on standing overnight. Recrystallization 3 times from benzene/ligroin, each time reducing the volume, gave 1.45 g of cream-colored powder, mp 155°–156° C. Elemental analysis gave a high carbon analysis and NMR showed the presence of benzene. The sample was dried at 100° C. in vacuo for 2 hr and resubmitted for elemental analysis.

Analysis: Calculated for $C_{12}H_{14}N_4O_2$: C, 58.53; H, 5.73; N, 22.75; Found: C, 58.58; H, 5.73; N, 22.78.

EXAMPLE 14

3-Butylamino-5-methyl-1H-pyrazole-4-carboxylic acid, ethyl ester

A stirred solution of 14.7 g (0.1 mole) of 4-butyl-3-thiosemicarbazide in 150 mL of absolute ethanol was treated with 16.5 g (0.1 mole) of ethyl 2-chloroacetoacetate. The reaction mixture while stirring at ambient temperature because progressively cloudy within 1 hr, then unexpectedly became clear. The reaction mixture was treated with 60 mL of 2N ethanolic hydrogen chloride and stirred at ambient temperature over the weekend. The reaction mixture was now cloudy, but cleared as the reaction mixture was heated to reflux. After 1 hr, the hot reaction mixture was filtered and concentrated in vacuo to give a yellow oil. Trituration of this oil with benzene/ligroin (50:50) gave 10.7 g of off-white solid. Recrystallization from benzene/ligroin gave 10.5 g of white powder, mp 138°–139.5° C. TLC (10% methanol/benzene; silica gel) showed 4 major spots and nmr analysis showed the presence of excess butyl radical. The reaction mixture product was then recrystallized from methanol/water (6.1 g). The filtrate was made basic with 3N sodium hydroxide solution and an additional 8 g (wet) of material was obtained. The 2 fractions were combined and recrystallized from benzene to give 11.2 g of fine white crystals which were dried at 82° C. under high vacuum, mp 109°–110° C.

NOTE: It was found that the hydrochloride salt of this compound is formed in nonaqueous solvents but dissociates in aqueous solution.

Analysis: Calculated for $C_{11}H_{19}N_3O_2$: C, 58.65; H, 8.50; N, 18.65; Found: C, 58.14; H, 8.54; N, 18.79.

EXAMPLE 15

3-Butylamino-5-methyl-1H-pyrazole-4-carboxylic acid, ethyl ester, sulfate[1:1]

A solution of 3-butylamino-5-methyl-1H-pyrazole-4-carboxylic acid ethyl ester (2 g in 20 mL of isopropyl ether) was treated dropwise with 1N sulfuric acid in 2-propanol. A turbid solution formed and an oil slowly separated and solidified. Recrystallization from isopropyl alcohol/isopropyl ether gave 2 g of fine white crystals, mp 81°–83° C. The sulfate salt, like the hydrochloride, dissociates in aqueous solution.

Analysis: Calculated for $C_{11}H_{21}SN_3O_6$: C, 40.86; H, 6.55; N, 12.99; Found: C, 40.62; H, 6.56; N:, 12.91.

EXAMPLE 16

3-[(2,6-Diethylphenyl)amino]-5-methyl-1H-pyrazole-4-carboxylic acid, ethyl ester, hydrochloride[1:1]

A stirred slurry of 9.4 g (0.05 mole) of 4-(2,6-diethylphenyl)-3-thiosemicarbazide in 75 mL of absolute ethanol was treated with 8.25 g (0.05 mole) of ethyl 2-chloroacetoacetate. The reaction mixture was stirred at ambient temperature as the color changed from white to yellow then to a greenish-white. The reaction mixture was treated with 40 mL of 2N ethanolic hydrogen chloride, heated at reflux for 1 hr then filtered hot. The filtrate upon cooling yielded a pale yellow solid, 16 g. Recrystallization from benzene/ligroin gave 15.5 g of white granular solid which was dried at 82+ C. under high vacuum for 3 hr, mp 167°–170° C. Elemental analysis and its $^1H$ NMR spectrum indicated the product was a hydrochloride salt.

Analysis: Calculated for $C_{17}H_{24}N_3O_2Cl$: C, 60.44; H, 7.16; N, 12.44; Found: C, 60.59; H, 7.16; N, 12.60.

EXAMPLE 17

3-[(2,4-Dimethylphenyl)amino]-5-methyl-1H-pyrazole-4-carboxylic acid, ethyl ester A stirred slurry of 10.8 g (0.06 mole) of 4-(2,4-dimethylphenyl)-3-thiosemicarbazide in 90 mL of absolute ethanol was treated with 9 g (0.066 mole) of ethyl 2-chloroacetoacetate. The mixture was stirred at ambient temperature for 1 hr under nitrogen atmosphere, then trated with 45 mL of 2N ethanolic hydrogen chloride and heated at reflux for 1 hr. The reaction mixture was filtered to remove amorphous sulfur and the filtrate concentrated in vacuo to give a yellow solid. Trituration with benzene gave 13.6 g of crude product which was crystallized from benzene/methanol (90:10) by reducing the volume in half while heating under a nitrogen atmosphere, to give 4.6 g of solid, mp 148°–171° C. Addition of ligroin to the filtrate gave, after 3 days, an additional 6.3 g of solid, mp 127°–129° C. Mass spectra of both samples were identical except that one showed hydrogen chloride present. Both compounds were dissolved in methanol/water and made basic with 3N sodium hydroxide. The solution became milky then a solid separated, 17 g (wet). After air drying for 3 days its final weight was 10.8 g. Recrystallization from benzene/ligroin gave 9.3 g of fine white crystals, mp 174.5°–176° C.

Analysis: Calculated for $C_{15}H_{19}N_3O_2$: C, 65.91; H, 7.01; N, 15.37; Found: C, 65.35; H, 6.99; N, 15.55.

EXAMPLE 18

3-[(4-Chloro-2-methylphenyl)amino]-5-methyl-1H-pyrazole-4-carboxylic acid, ethyl ester A stirred slurry of 11.4 g (0.053 mole) of 4-(4-chloro-2-methylphenyl)-3-thiosemicarbazide in 80 mL of absolute ethanol was treated with 9.6 g (0.0583 mole) of ethyl 2-chloroacetoacetate then stirred for 1 hr at ambient temperature. The reaction mixture was treated with 40 mL of 2N ethanolic hydrogen chloride, heated to reflux, then allowed to stir ~16 hr at ambient temperature. The reaction mixture was again heated to reflux to dissolve most of the material and filtered hot to remove the amorphous sulfur. The filtrate was concentrated in vacuo. The yellow solid obtained was recrystallized from methanol/benzene to give 9.5 g of crystalline product, mp 146°–177° C. Addition of ligroin to the filtrate gave after 6 hr an additional 3.8 g, mp 170°–183° C. Both fractions were combined in acetone/water and made basic with 3N sodium hydroxide. The milky mixture was heated until a clear solution was obtained and upon cooling, the product crystallized, 34 g (wet). The product was air dried and recrystallized from benzene to give 9 g of fine white crystals, mp 156°–187° C.

Analysis: Calculated for $C_{14}H_{16}N_3O_2Cl$: C, 57.24; H, 5.50; N, 14.30; Found: C, 57.23; H, 5.49; N, 14.36.

EXAMPLE 19

3-[(2,4-Dichlorophenyl)amino]-5-methyl-1H-pyrazole-4-carboxylic acid, ethyl ester A slurry of 9.5 g (0.04 mole) of 4-(2,4-dichlorophenyl)-3-thiosemicarbazide in 60 mL of absolute ethanol was treated with 6.7 g (0.04 mole) of ethyl 2-chloroacetoacetate then stirred for 1.5 hr at ambient temperature. The reaction mixture was treated with 30 mL of 2N ethanolic hydrogen chloride, heated at reflux for 2 hr and allowed to cool ~16 hr. The reaction mixture was heated to reflux to dissolve most of the material and filtered to remove the amorphous sulfur. Upon cooling the filtrate yielded 3.7 g of tan product. The residue was concentrated in vacuo to give 4.2 g of crude yellow solid. All the reaction mixture materials were dissolved in methanol, treated with 3N sodium hydroxide, then diluted with water under a curd-like material separated. This crude yellow-tan solid, 28 g (wet) was allowed to air dry then recrystallized from 2-propyl alcohol to give two batches of solid, 4.3 g of fine white needles, mp 215°–217° C. and 2.2 g of fine pale beige needles, mp 214°–215° C. Comparison TLC of both compounds (10% methanol/benzene; silica gel) showed them to be identical. They were combined for analysis.

Analysis: Calculated for $C_{13}H_{13}N_3O_2Cl_2$: C, 49.70; H, 4.17; N, 13.38; Found: C, 49.72; H, 4.17; N, 13.49.

EXAMPLE 20

3-[(2-Chloro-6-methylphenyl)amino]-5-methyl-1H-pyrazole-4-carboxylic acid, ethyl ester A slurry of 21.5 g (0.1 mole) of 4-(2-chloro-6-methylphenyl)-3-thiosemicarbazole in 100 mL of absolute ethanol was treated with 16.5 g (0.1 mole) of ethyl 2-chloroacetoacetate and stirred at ambient temperature for 1 hr. The yellow mixture was treated with 50 mL of 2N ethanolic hydrogen chloride and heated at reflux until the reaction mixture was a clear red-brown color (2.5 hr). The reaction mixture was filtered and the filtrate concentrated in vacuo to give 43 g of crude yellow solid. The crude solid was dissolved in acetone, made basic with 40 mL of 3N sodium hydroxide, filtered to remove some insoluble material and diluted with water to precipitate the product, 38 g (wet). After air drying, it was recrystallized from acetone to give 14.6 g of white crystalline product, mp 158°–159° C.

Analysis: Calculated for $C_{14}H_{16}N_3O_2Cl$: C, 57.24; H, 5.50; N, 14.30; Found: C, 57.26; H, 5.50; N, 14.45.

EXAMPLE 21

3-[(4-Bromo-2,6-dimethylphenyl)amino]-5-methyl-1H-pyrazole-4-carboxylic acid, ethyl ester A mixture of 14.6 g (0.06 mole) of 4-(4-bromo-2,6-dimethylphenyl)-3-thiosemicarbazide and 9.93 g (0.06 mole) of ethyl 2-chloroacetoacetate in 60 mL of absolute ethanol was stirred under nitrogen atmosphere for 2 hr, treated with 30 mL of 2N ethanolic hydrogen chloride and heated at reflux until the reaction mixture cleared (3 hr). The reaction mixture was filtered hot then concentrated in vacuo to give an orange solid which, when triturated with warm benzene/ligroin (50:50) and filtered gave 10.8 g of slightly orange crystalline product. The filtrate upon standing for ~16 hr gave an additional 4.4 g of yellow crystals which became white when washed with warm acetone. The 2 fractions were combined and recrystallized from benzene/ligroin to give 10.35 g of fine white crystalline rods, mp 171°–199° C. (with degassing). An NMR analysis showed the solid to be a salt with some solvent present; mass spectra confirmed the presence of hydrogen chloride. After drying at 82° C. under high vacuum, there was left 9.56 g, mp 168°–196° C. A broad melting point range suggested that it may be a mixture of free base and salt; therefore, it was dissolved in methanol/water along with other reaction mixture material, made basic with 3N sodium hydroxide and extracted with 5×60 mL of methylene chloride. The extracts were combined, washed with water, dried over magnesium sulfate and concentrated in vacuo to give a dark yellow solid. Recrystallization from benzene/ligroin then from benzene gave 10.7 g of white granular powder, mp 184°–185° C.

Analysis: Calculated for $C_{15}H_{18}N_3O_2Br$: C, 51.15; H, 5.15; N, 11.93; Found: C, 51.19; H, 5.09; N, 12.09.

EXAMPLE 22

5-Methyl-3-(methylamino)-1H-pyrazole-4-carboxylic acid, ethyl ester

A stirred mixture of 42 g (0.4 mole) of 4-methyl-3-thiosemicarbazide and 65.8 g (0.4 mole) of ethyl 2-chloroacetoacetate in 200 mL of absolute ethanol became exothermic after mixing, warming the mixture nearly to reflux. After stirring for 1 hr the reaction mixture was cooled to ambient temperature. The yellow-green slurry was treated with 200 mL of 2N ethanolic hydrogen chloride and was allowed to stir at ambient temperature for ~72 hr. The orange-red slurry was heated to reflux and diluted with 1200 mL of hot absolute ethanol leaving only amorphous sulfur which was removed by filtration. The solvent was evaporated in vacuo leaving a crude orange solid which was triturated with refluxing acetone to give 45.6 g of white granular product. Recrystallization from absolute ethanol gave upon cooling a fine granular precipitate; however, after 5 hr fine white needles formed, suggesting the presence of 2 different products. The solid material as well as reaction mixture residues were combined in methanol/water and made basic with 3N sodium hydroxide. The basic mixture was extracted with 3×200 mL of methylene chloride. The extracts were combined, washed with water (50 mL), dried over magnesium sulfate and concentrated on a rotary evaporator to give a yellow solid. Recrystallization from acetone gave 19.2 g of fine white needles, mp 161°–162° C. A second crude crop of 9 g was obtained from the filtrate.

Analysis: Calculated for $C_8H_{13}N_3O_2$: C, 52.45; H, 7.15; N, 22.94; Found: C, 52.71; H, 7.24; N, 23.25.

EXAMPLE 23

5-Methyl-3-[(2-propenyl)amino]-1H-pyrazole-4-carboxylic acid, ethyl ester, hydrochloride[1:1]

A mixture of 26.24 g (0.2 mole) of 4-(2-propenyl)-3-thiosemicarbazide and 32.9 g (0.2 mole) of ethyl 2-chloroacetoacetate in 150 mL of absolute ethanol was stirred under nitrogen atmosphere for 1.5 hr, treated with 100 mL of 2N ethanolic hydrogen chloride and heated at reflux for 1.5 hr. The reaction mixture was stirred at ambient temperature for ~72 hr, heated to reflux and filtered to remove the amorphous sulfur. The filtrate was concentrated in vacuo to give a deep red oil which crystallized on trituration with acetone to give 29 g of product. Recrystallization from acetone gave 21 g of needle-like crystals with yellow. A second recrystallization from benzene gave 15.8 g of fine white needles, mp 133°–134° C. A rework of the filtrate from both recrystallizations gave an additional 7 g of crude product.

Analysis: Calculated for $C_{10}H_{16}N_3O_2Cl$: C, 48.88; H, 6.56; N, 17.10; Found: C, 49.20; H, 6.61; N, 17.35.

EXAMPLE 24

3-(Ethylamino)-5-methyl-1H-pyrazole-4-carboxylic acid, ethyl ester, hydrochloride[1:1]

A mixture of 47.68 g (0.4 mole) of 4-ethyl-3-thiosemicarbazide and 65.8 g (0.4 mole) of ethyl 2-chloroacetoacetate was stirred under nitrogen atmosphere for 1.5 hr at ambient temperature then treated with 200 mL of 2N ethanolic hydrogen chloride. The mixture was stirred for ~72 hr, filtered to remove the amorphous sulfur, and the solvent was removed in vacuo to give a deep amber oil which solidified. Recrystallization from acetone gave 27 g of crude product which was recrystallized from benzene/petroleum ether to give 23.5 g of fine white crystals, mp 140°–148° C. Rework of the filtrate gave an additional 17.5 g of crude product.

Analysis: Calculated for $C_9H_{16}N_3O_2Cl$: C, 46.26; H, 6.90; N, 17.98; Found: C, 46.40; H, 6.91; N, 18.37.

EXAMPLE 25

3-(Cyclohexylamino)-5-methyl-1H-pyrazole-4-carboxylic acid, ethyl ester, hydrochloride[1:1]

A mixture of 34.7 g (0.2 mole) of 4-cyclohexyl-3-thiosemicarbazide and 32.9 g (0.2 mole) of ethyl 2-chloroacetoacetate in 350 mL of absolute ethanol was stirred under nitrogen atmosphere at ambient temperature for 2 hr, treated with 100 mL of 2N ethanolic hydrogen chloride and heated at reflux for 2 hr. The hot reaction mixture was filtered to remove an amorphous solid. The product persistently crystallized in the filter. The product was recrystallized from acetone and recovered by decating off hot acetone solvent and washing the residue with cold acetone to give 27 g of large, off-white crystals, mp 178°–182° C.

Analysis: Calculated for $C_{13}H_{22}N_3O_2Cl$: C, 54.26; H, 7.71; N, 14.60; Found: C, 54.27; H, 7.71; N, 14.75.

EXAMPLE 26

5-Methyl-3-[(phenylmethyl)amino]-1H-pyrazole-4-carboxylic acid, ethyl ester

A mixture of 18 g (0.106 mole) of 4-phenylmethyl-3-thiosemicarbazide and 18 g (0.11 mole) of ethyl 2-chloroacetoacetate in 200 mL of absolute ethanol was stirred at ambient temperature for 1.5 hr then heated at reflux for 2 hr. The clear red-orange reaction mixture was filtered hot to remove amorphous sulfur and concentrated in vacuo to give a crude yellow paste. Trituration with acetone gave 22.8 g of yellow crystalline product. Recrystallization of a 6 g portion from acetone gave 2 products with melting points of 138°–140° C. and 200°–205° C. A sample was dissolved in methanol/water and converted to the free base with 3N sodium hydroxide. The resulting solid was recrystallized from acetone to give 3.3 g of fine white crystals which were dried at 98° C. for 18 hr under reduced pressure (mp 149°–159° C.).

Analysis: Calculated for $C_{14}H_{17}N_3O_2$: C, 64.84; H, 6.61; N, 16.21; Found: C, 64.45; H, 6.58; N, 16.24.

EXAMPLE 27

3-Amino-5-methyl-1H-pyrazole-4-carboxylic acid, ethyl ester, hydrochloride[1:1]

A stirred mixture of 9.1 g (0.1 mole) of 3-thiosemicarbazide and 1 mL of concentrated hydrochloride acid in 150 mL of absolute ethanol was cooled to 0° C. in an ice bath and 16.5 g (0.1 mole) of ethyl 2-chloroacetoacetate was added dropwise. The thiosemicarbazide dissolved as the reaction mixture was allowed to slowly come to ambient temperature, it then became yellow and a new precipitate formed. The reaction mixture was heated at reflux for 3 hr. All the material had not dissolved so the reaction mixture was diluted with water and made acidic with 3N hydrochloric acid to dissolve all the solids but sulfur. After filtering, the filtrate was concentrated in vacuo leaving an orange-red oil which slowly crystallized when acetone was added to give 11.5 g of orange powder, mp 186°–188° C., with decomposition.

Analysis: Calculated for $C_7H_{11}N_3O_2$: C, 40.89; H, 5.88; N, 20.43; Found: C, 40.64; H, 5.54; N, 20.59.

EXAMPLE 28

3-[(1-Adamantyl)amino]-5-methyl-1H-pyrazole-4-carboxylic acid, ethyl ester

A mixture of 11.26 g (0.05 mole) of 4-(1-adamantyl)-3-thiosemicarbazide and 8.2 g (0.05 mole) of ethyl 2-chloroacetoacetate in 100 mL of absolute ethanol was stirred at ambient temperature for 2 days, heated at reflux for 2 hr, filtered hot to remove the sulfur, and concentrated in vacuo to give 19 g of white solid residue. The solid was dissolved in methanol/benzene and washed with 3N sodium hydroxide to convert all the material to the free base. The benzene layer was separated, washed with water, dried over magnesium sulfate and concentrated to give a solid residue. After trying to recrystallize the residue from various solvents and solvent mixtures, all 9.5 g was dissolved in acetic acid and treated with concentrated hydrochloric acid which gave 6.8 g of hydrochloride salt when concentrated in vacuo. Recrystallization from acetone/diethyl ether gave 2.5 g of fine white crystals, mp 151°–180° C. Rework of the filtrate gave 5 additional fractions. TLC (10% methanol/benzene; silica gel) showed that only 2 fractions were pure. They were combined (7.6 g) and recrystallized from ethyl acetate to give 4.2 g of fine white crystals, mp 190°–203° C. (red melt).

Analysis: Calculated for $C_{17}H_{26}ClN_3O_2$: C, 60.08; H, 7.71; N, 12.36; Found: C, 60.31; H, 7.74; N, 12.57.

EXAMPLE 29

3-Dimethylamino-5-methyl-1H-pyrazole-4-carboxylic acid, ethyl ester, hydrochloride[1:1]

A stirred slurry of 2.5 g (0.013 mole) of 4,4-dimethyl-3-thiosemicarbazide in 50 mL of absolute ethanol was treated with 2.1 g (0.013 mole) of ethyl 2-chloroacetoacetate added at a rapid rate under nitrogen atmosphere. The reaction mixture turned yellow immediately, cleared, became cloudy and finally became a clear orange solution within 5 minutes. The reaction mixture was stirred at ambient temperature for ~72 hr, heated to reflux, filtered hot, and concentrated in vacuo to give a yellow oil which solidified. Trituration with benzene gave 3 g of tan solid. After 3 recrystallizations from benzene, 1.8 g of fine pale beige crystalline product was obtained, mp 135°–139° C. After drying at 98° C. under reduced pressure for 3 hr, mp 137°–139° C.

Analysis: Calculated for $C_9H_{16}ClN_3O_2$: C, 46.26; H, 6.90; N, 17.98; Found: C, 46.05; H, 6.91; N, 18.09.

EXAMPLE 30

5-Methyl-3-[(2-phenylethyl)amino]-1H-pyrazole-4-carboxylic acid, ethyl ester

A stirred slurry of 33.1 g (0.17 mole) of 4-phenylethyl-3-thiosemicarbazide in 500 mL of absolute ethanol under nitrogen atmosphere was treated with 29 g (0.17 mole) of ethyl 2-chloroacetoacetate, stirred at ambient temperature for ~72 hr, heated to reflux to dissolve most materials, and filtered hot. The filtrate was concentrated in vacuo to give a reddish oil, 71 g. The residue was chromatographed on 800 g Florosil® and eluted first with benzene to remove a yellow band (sulfur) followed by an acetone/benzene gradient which gave two main fractions. These two fractions were combined, and concentrated to give a yellow oil which solidified. Recrystallization (twice) from ligroin gave a fluffy white crystalline product, with small spots of green-yellow color, 12.1 g, mp 138°–139° C.

Analysis: Calculated for $C_{15}H_{19}N_3O_2$: C, 65.91; H, 7.01; N, 15.37; Found: C, 65.78; H, 6.99; N, 15.42.

EXAMPLE 31

3-Heptylamino-5-methyl-1H-pyrazole-4-carboxylic acid, ethyl ester, hydrochloride [1:1]

A stirred solution of 30.3 g (0.16 mole) of 4-heptyl-3-thiosemicarbazide in 500 mL of absolute ethanol under nitrogen atmosphere was treated with the rapid addition of 26.3 g (0.16 mmole) of ethyl 2-chloroacetoacetate, stirred at ambient temperature for ~16 hr, heated at reflux for 3 hr and filtered hot. Concentration of the filtrate in vacuo gave a deep red oil. The oil solidified on standing for ~16 hr and was recrystallized from 2-propyl alcohol to give 15 g of fine white crystals, mp 83°–84° C.

Analysis: Calculated for $C_{14}H_{26}ClN_3O_2$: C, 55.35; H, 8.63; N, 13.83; Found: C, 55.47; H, 8.64; N, 13.91.

EXAMPLE 32

3-[(1,1-Dimethylethyl)amino]-5-methyl-1H-pyrazole-4-carboxylic acid, ethyl ester A solution of 25 g (0.17 mole) of 4-(1,1-dimethylethyl)-3-thiosemicarbazide in 85 mL of 2N ethanolic hydrogen chloride was cooled to 0° C. with an ice bath and while stirring under nitrogen atmosphere, 28 g (0.17 mole) of ethyl 2-chloroacetoacetate was added dropwise. The reaction mixture was allowed to come to room temperature while stirring for 16 hr. The pale yellow solution was then refluxed for 2 hr during which a film of sulfur deposited on the sides of the flask. The reaction mixture was cooled to room temperature and the sulfur removed by filtration. The filtrate was concentrated in vacuo to give 39 g of pale yellow oil which was dissolved in ligroin and, after standing at ~7°–10° C. for ~60 hr, yielded 20.5 g of large crystals, mp 118°–119° C. An additional 6.1 g of crude material was obtained by reworking the residues.

Analysis: Calculated for $C_{10}H_{19}N_3O_2$: C, 58.65; H, 8.50; N, 18.65; Found: C, 58.66; H, 8.54; N, 18.72.

EXAMPLE 33

3-(Cycloheptylamino)-5-methyl-1H-pyrazole-4-carboxylic acid, ethyl ester, hydrochloride [1:1]

A solution of 11.6 g (0.0619 mole) of 4-cycloheptyl-3-thiosemicarbazide in 100 mL of tetrahydrofuran was stirred under nitrogen atmosphere while 10.2 g (0.062 mole) of ethyl 2-chloroacetoacetate was added. The reaction mixture quickly turned yellow and slowly became exothermic to boiling. The reaction mixture was refluxed for 1.5 hr, filtered (to remove amorphous sulfur), and concentrated in vacuo to give yellow granular solid, 19.7 g. Several attempts at recrystallization of the material from various solvents resulted in 4 fractions all having melting points in the range of 157°–160° C. These were combined (12 g) and recrystallized from methyl isobutyl ketone, after treating with charcoal, to give 10.3 g of product. After drying at 82° C. under vacuum for 15 hr the weight was reduced to 9.8 g with mp 155°–161° C.

Analysis: Calculated for $C_{14}H_{24}N_3O_2Cl$: C, 55.71; H, 8.02; N, 13.92; Found: C, 55.85; H, 7.94; N, 13.89.

EXAMPLE 34

3-(Cyclopentylamino)-5-methyl-1H-pyrazole-4-carboxylic acid, ethyl ester hydrochloride [1:1]

A stirred slurry of 8.3 g (0.052 mole) of 4-cyclopentyl-3-thiosemicarbazide in 50 mL of absolute ethanol under nitrogen atmosphere was treated with 8.6 g (0.052 mole) of ethyl 2-chloroacetoacetate. The reaction mixture which, after filtering, turned pale yellow, was stirred for 18 hr at ambient temperature, treated with 20 mL of 2N ethanolic hydrogen chloride and heated at reflux for 1 hr. The reaction mixture was filtered hot and the filtrate concentrated in vacuo to a yellow-orange solid. Most of the solid was dissolved in 100 mL of hot absolute ethanol. The mixture was filtered, and when the filtrate was treated with dipropyl ether (150 mL) a precipitate formed which was collected by filtration to give 11.7 g of crude product. Recrystallization from benzene/ligroin with charcoal treatment gave 7.6 g of fine white fluffy needles, mp 175°–177° C.

Analysis: Calculated for $C_{12}H_{20}N_3O_2Cl$: C, 52.65; H, 7.36; N, 15.35; Found: C, 52.83; H, 7.33; N, 15.41.

EXAMPLE 35

3-(Cyclopropylamino)-5-methyl-1H-pyrazole-4-carboxylic acid, ethyl ester hydrochloride [1:1]

A stirred slurry of 10.4 g (0.079 mole) of 4-cyclopropyl-3-thiosemicarbazide under nitrogen atmosphere was treated with 13 g (0.079 mole) of ethyl 2-chloroacetoacetate, stirred at ambient temperature for 1 hr, treated with 30 mL of 2N ethanolic hydrogen chloride and heated to reflux. The reaction mixture was allowed to cool to ambient temperature while stirring for ~72 hr. the sulfur residue was removed by filtration and the filtrate concentrated in vacuo to an orange oil which solidified. Recrystallization twice from acetone gave 7.4 g of large blade-like crystals, after drying for 2 hr at 98° C. under reduced pressure, mp 147°–148.5° C. The filtrates gave an additional 6 g of crude product. The 2 solids were combined and recrystallized from methyl ethyl ketone to give 6.3 g of white crystalline powder, mp 151°–152° C.

Analysis: Calculated for $C_{10}H_{16}N_3O_2Cl$: C, 48.88; H, 6.56; N, 17.10; Found: C, 48.72; H, 6.55; N, 17.28.

EXAMPLE 36

5-Methyl-3-(propylamino)-1H-pyrazole-4-carboxylic acid, ethyl ester, hydrochloride [1:1]

A stirred solution of 10.1 g (0.076 mole) of 4-propyl-3-thiosemicarbazide in 50 mL of absolute ethanol under nitrogen atmosphere was treated with 12.5 g (0.076 mole) of ethyl 2-chloroacetoacetate. After stirring at ambient temperature for 3 hr, it was treated with 20 mL of 2N ethanolic hydrogen chloride, heated at reflux for 45 minutes and cooled to ambient temperature while stirring for ~72 hr. The reaction mixture was filtered to remove the amorphous sulfur and the filtrate concentrated in vacuo to give an orange paste. Recrystallization from a small amount of cold acetone gave the crude product, which was recrystallized from methyl ethyl ketone to give 11.8 g of fine pale beige needles, mp 154°–161° C. TLC (20% methanol/benzene; silica gel) showed one major spot and 2 minor ones. Recrystallized from toluene gave 9.5 g of fine white crystals, mp 155°–161° C.

Analysis: Calculated for $C_{10}H_{18}N_3O_2Cl$: C, 48.49; H, 7.32; N, 16.96; Found: C, 48.76; H, 7.36; N, 17.19.

EXAMPLE 37

5-Methyl-3-[(1-methylpropyl)amino]-1H-pyrazole-4-carboxylic acid, ethyl ester, hydrochloride [1:1]

A stirred solution of 5.1 g (0.035 mole) of 4-(2-butyl)-3-thiosemicarbazide in 40 mL of absolute ethanol was treated with 5.7 g (0.035 mole) of ethyl 2-chloroacetoacetate and stirred at ambient temperature for 3 hr. The mixture was treated with 20 mL of 2N ethanolic hydrogen chloride, heated at reflux for 1 hr and stirred for ~16 hr at ambient temperature. The reaction mixture after filtering and concentrating in vacuo gave a crude orange solid. A second reaction mixture was prepared with 8.0 g (0.054 mole) of crude 4-(2-butyl)-3-thiosemicarbazide, 50 mL of absolute ethanol, 8.9 g (0.054 mole) of ethyl 2-chloroacetoacetate, and 25 mL of 2N ethanolic hydrogen chloride as described above and gave a crude orange solid. The TLC of both crude products (10% methanol/benzene; silica gel) were identical. Recrystallization of the first batch from acetone/isopropyl ether gave 4 g of fine white crystals, mp 147°–148.5° C. Recrystallization of the second batch from benzene/ligroin gave 2.5 g of pale yellow crystalline product, mp 146°–148.5° C. The 2 solids were combined (6.5 g) and recrystallized from 200 mL of acetone/isopropyl ether (3:1) to give 3.6 g of white fluffy crystals, mp 147°–149° C.

Analysis: Calculated for $C_{11}H_{20}N_3O_2Cl$: C, 50.48; H, 7.70; N, 16.05; Found: C, 50.63; H, 7.70; N, 16.19.

EXAMPLE 38

5-Methyl-3-(pentylamino)-1H-pyrazole-4-carboxylic acid, ethyl ester

A stirred solution of 25.8 g (0.16 mole) of 4-pentyl-3-thiosemicarbazide in 150 mL of tetrahydrofuran was treated with 26.4 g (0.16 mole) of ethyl 2-chloroacetoacetate, stirred at ambient temperature for 2 hr, heated at reflux for 4 hr, and stirred for ~16 hr at ambient temperature. The reaction mixture contained amorphous material and large yellow crystals, which dissolved on heating at reflux for 1 hr. Upon cooling, large yellow crystals separated and were removed by filtration (sulfur). The filtrate was diluted with ice water, made acidic with 6N sulfuric acid and filtered to remove additional sulfur. The filtrate was adjusted to pH 6 with sodium carbonate and a total of 32.2 g of precipitated product was collected in 3 fractions. All the material was chromatographed twice on silica gel without purification, first by eluting with methylene chloride and the second time by eluting with benzene. A third column of 800 g of silica gel was eluted with isopropyl ether to give an orange oil which was not the product, then eluted with 50/50 isopropyl ether/methylene chloride. The product crystallized from the second eluent to give 7.8 g of white crystalline product after washing with isopropyl ether to remove a yellow color, mp 117°–119° C.

Analysis: Calculated for $C_{12}H_{21}N_3O_2$: C, 60.78; H, 8.85; N, 17.56; Found: C, 60.24; H, 8.88; N, 17.59.

EXAMPLE 39

3-(Hexylamino)-5-methyl-1H-pyrazole-4-carboxylic acid, ethyl ester, hydrochloride [1:1]

A stirred solution of 15.8 g (0.091 mole) of 4-hexyl-3-thiosemicarbazide in 150 mL of absolute ethanol under nitrogen atmosphere was treated with 14.8 g (0.091 mole) of ethyl 2-chloroacetoacetate, stirred for 2.5 hr at ambient temperature, treated with 50 mL of 2N ethanolic hydrogen chloride, heated at reflux for 1 hr, and stirred at ambient temperature ~16 hr. The reaction mixture was heated to dissolve most of the solids, filtered to remove the insoluble sulfur and concentrated in vacuo to give a deep red-orange oil. After standing for 3 weeks at ambient temperature, the oil began to crystallize. Trituration with ethyl acetate and filtration gave 13 g of crude product, which was recrystallized from acetone/diethyl ether to give 7.5 g of white granular product, mp 108°-109° C.

Analysis: Calculated for $C_{13}H_{24}N_3O_2Cl$: C, 53.88; H, 8.35; N, 14.50; Found: C, 53.71; H, 8.38; N, 14.71.

EXAMPLE 40

3-(Cyclooctylamino)-5-methyl-1-H-pyrazole-4-carboxylic acid, ethyl ester, hydrochloride [1:1]

A stirred slurry of 18.7 g (0.093 mole) of 4-cyclooctyl-3-thiosemicarbazide in 150 mL of absolute ethanol under nitrogen atmosphere was treated with 16.5 g (0.1 mole) of ethyl 2-chloroacetoacetate, stirred at ambient temperature for 1.5 hr, treated with 50 mL of 2N ethanolic hydrogen chloride and heated at reflux for ~16 hr. The yellow-brown reaction mixture was filtered and concentrated in vacuo to a dark oil which solidified. Trituration of the crude product with warm acetone removed most of the color to give 17.9 g of product. Recrystallization from methyl ethyl ketone/isopropyl ether followed by recrystallization from methyl ethyl ketone gave 7.1 g of crystalline product, mp 161°-166° C. which was dried at 82° C. under reduced pressure for 3 hr (mp, 168°-171° C.).

Analysis: Calculated for $C_{15}H_{26}N_3O_2Cl$: C, 57.04; H, 8.30; N, 13.30; Found: C, 56.98; H, 8.33; N, 13.48.

EXAMPLE 41

5-Methyl-3-[(2-methylbutyl)amino]-1H-pyrazole-4-carboxylic acid, ethyl ester, hydrochloride [1:1]

A stirred pale yellow solution of 14.3 g (0.089 mole) of 4-(2-methylbutyl)-3-thiosemicarbazide in 50 mL of absolute ethanol was cooled to −10° C. in an ice/methanol bath and treated under nitrogen atmosphere with 15 g (0.09 mole) of ethyl 2-chloroacetoacetate. The reaction mixture was stirred for 2 hr at 15° C., heated to reflux, treated with 50 mL of 2N ethanolic hydrogen chloride and after 1 hr at reflux, filtered to remove the amorphous sulfur. The filtrate was concentrated in vacuo to give a deep red oil, 26.8 g, which failed to crystallize. The TLC (10% methanol/methylene chloride; silica gel) showed at least 10 spots. A sample (9 g) of the oil was dissolved in isopropyl ether, and extracted with 6N sulfuric acid. The combined aqueous acid portions were cooled in an ice bath and neutralized with base to give a yellow oil. This oil was extracted into methylene chloride which was dried over magnesium sulfate and concentrated to give 5.7 g of yellow oil. The oil was dissolved in benzene, treated with 30 g of Florisil ®, stirred for ~16 hr, and filtered. The Florisil ® was washed with methylene chloride until the effluent was clear, and then washed with methanol until clear. The methanol fractions were combined, concentrated in vacuo to give 3.5 g of pale yellow oil which was dissolved in diethyl ether, cooled to −50° C. and filtered to remove some insoluble Florisil ®. The filtrate was treated with ethereal hydrogen chloride to give a fine crystalline product, 4.1 g. Recrystallization from isopropyl ether gave 2.8 g of silver plate-like crystals, mp 130°-133° C.

Analysis: Calculated for $C_{12}H_{22}N_3O_2Cl$: C, 52.26; H, 8.04; N, 15.24; Found: C, 52.23; H, 8.09; N, 15.43.

EXAMPLE 42

5-Methyl-3-[(1,1,3,3,-tetramethylbutyl)amino]-1H-pyrazole-4-carboxylic acid, ethyl ester, hydrochloride [1:1]

A stirred solution of 19.5 g (0.096 mole) of 4-(1,1,3,3-tetramethylbutyl)-3-thiosemicarbazide in 100 mL of absolute ethanol under nitrogen atmosphere was treated with 16.5 g (0.1 mole) of ethyl 2-chloroacetoacetate (slightly exothermic). The reaction mixture was stirred at ambient temperature for 1 hr, treated with 50 mL of 2N ethanolic hydrogen chloride, heated at reflux for 1 hr and stirred for ~72 hr at ambient temperature. A precipitate of amorphous sulphur indicated that the reaction was complete. The sulfur wwas removed by filtration, the filtrate concentrated in vacuo and the residue when triturated with hot acetone gave a pale yellow insoluble crystalline solid. The supernate fractions were combined and yielded 3.5 g of fine white crystals on cooling, mp 167°-168° C. After 24 hr an additional crop of crystals was obtained from the acetone filtrate. Mass spectra showed all the solids to be the expected product. TLC (10% methanol/benzene; silica gel) showed 1 major spot for each fraction.

Analysis: Calculated for $C_{15}H_{28}N_3O_2Cl$: C, 56.68; H, 8.88; N, 13.22; Found: C, 56.68; H, 8.85; N, 13.33.

EXAMPLE 43

3-Dibutylamino)-5-methyl-1H-pyrazole-4-carboxylic acid, ethyl ester, hydrochloride [1:1]

A stirred solution of 14.3 g (0.07 mole) of 4,4-di-n-butyl-3-thiosemicarbazide in 100 mL of absolute ethanol was cooled to 10° C. under nitrogen atmosphere, treated with 11.6 g (0.07 mole) of ethyl 2-chloroacetoacetate, warmed to 60° C., then cooled to ambient temperature and stirred for 18 hr. The reaction mixture was heated to reflux in order to dissolve the precipitate, filtered to remove amorphous sulfur and concentrated in vacuo to give a solid. The solid was recrystallized from acetone to yield 8 g of white crystalline product, mp 159°-162° C., as the hydrochloride salt.

Analysis: Calculated for $C_{15}H_{28}ClN_3O_2$: C, 56.68; H, 8.88; N, 13.22; Found: C, 56.67; H, 8.97; N, 13.25.

EXAMPLE 44

5-Methyl-3-(4-morpholinyl)-1H-pyrazole-4-carboxylic acid, ethyl ester, hydrochloride [1:1]

A stirred slurry of 6.3 g (0.039 mole) of 4-morpholinecarbothioic acid hydrazide in 75 mL of absolute ethanol under nitrogen atmosphere was treated with 6.43 g (0.039 mole) of ethyl 2-chloroacetoacetate and the exothermic reaction mixture stirred at ambient temperature for 18 hr. The major portion of reaction mixture solids were dissolved by heating to reflux, the sulfur residue removed by filtration and the filtrate concentrated in vacuo to a solid, which was crystallized from 2-propyl alcohol to yield 5.5 g of white crystalline needles, mp 165°–173° C., as the hydrochloride salt.

Analysis: Calculated for $C_{11}H_{18}N_3O_3Cl$: C, 47.92; H, 6.58; N, 15.24; Found: C, 47.68; H, 6.60; N, 15.28.

EXAMPLE 45

3-(Cyclohexylamino)-5-methyl-1H-pyrazole-4-carboxylic acid

A solution of 2 g (0.007 mole) of 3-cyclohexylamino-5-methyl-1H-pyrazole-4-carboxylic acid, ethyl ester hydrochloride [1:1] in 30 mL of ethanol was treated with 5 mL of 50% sodium hydroxide solution, 20 mg of tetrabutylammonium bromide and stirred rapidly while heating at reflux. After 20 hr the reaction mixture was diluted with ice water, extracted with 6×100 mL of isopropyl ether, the pH adjusted to 7 with concentrated sulfuric acid and to pH 5.5 with 10 g of sodium dihydrogen phosphate. The fine precipitate was collected by filtration to give 0.6 g of beige powder, mp 162°–163° C. (degasses).

Analysis: Calculated for $C_{11}H_{17}N_3O_2$: C, 59.17; H, 7.68; N, 18.82; Found: C, 59.13; H, 7.67; N, 18.72.

EXAMPLE 46

3-(Cyclohexylmethylamino)-5-methyl-1H-pyrazole-4-carboxylic acid, ethyl ester, hydrochloride [1:1]

A stirred slurry of 11.6 g (0.062 mole) of 4-cyclohexyl-4-methyl-3-thiosemicarbazide in 60 mL of absolute ethanol under nitrogen atmosphere was treated with 10.2 g (0.062 mole) of ethyl 2-chloroacetoacetate, stirred at ambient temperature for 4 hr, treated with 35 mL of 2N ethanolic hydrogen chloride, and heated at reflux until clear. The hot reaction mixture was filtered to remove amorphous sulfur and the red filtrate concentrated in vacuo. The oily residue which crystallized when triturated with acetone gave 14 g of crude product. Recrystallization from 2-propyl alcohol/2-propyl ether gave 7.9 g of crystalline product, mp 156°–158° C., as the hydrochloride salt.

Analysis: Calculated for $C_{14}H_{23}N_3O_2Cl$: C, 55.71; H, 8.02; N, 13.92; Found: C, 55.66; H, 8.04; N, 13.94.

EXAMPLE 47

3-(Cyclopentylmethylamino)-5-methyl-1H-pyrazole-4-carboxylic acid, ethyl ester, hydrochloride [1:1]

A stirred slurry of 8.4 g (0.049 mole) of 4-cyclopentyl-4-methyl-3-thiosemicarbazide in 50 mL of absolute ethanol was treated with 8.1 g (0.049 mole) of ethyl 2-chloroacetoacetate, stirred at ambient temperature for 18 hr, treated with 25 mL of 2N ethanolic hydrogen chloride and heated at reflux for 2 hr. The hot solution was filtered to remove amorphous sulfur and concentrated to a red oil which gave a crude solid product when triturated with acetone. After four recrystallizations; methyl ethyl ketone/2-propyl ether (twice), acetonitrile/acetone and finally from acetonitrile, there was obtained 3.2 g of crystalline product, mp 144°–146° C., as the hydrochloride salt.

Analysis: Calculated for $C_{13}H_{22}N_3O_2Cl$: C, 54.26; H, 7.71; N, 14.60; Found: C, 54.06; H, 7.70; N, 14.59.

EXAMPLE 48

3-[[3-(Dimethylamino)propyl]amino]-5-methyl-1H-pyrazole-4-carboxylic acid ethyl ester hydrochloride [1:2]

A stirred solution of 7.05 g (0.04 mole) of 4-(3-dimethylaminopropyl)-3-thiosemicarbazide in 50 mL of absolute ethanol under nitrogen atmosphere was treated with 40 mL of 2N ethanolic hydrogen chloride and then with 6.6 g (0.04 mole) of ethyl 2-chloroacetoacetate, stirred at ambient temperature for 2 hr and heated at reflux for 5 hr. The reaction mixture was filtered hot to remove some crystalline sulfur and the filtrate solidified on cooling to give 8.3 g of crude product. After 5 recrystallizations from methyl ethyl ketone/methanol with charcoal treatment of the final recrystallization, a crystalline product was obtained, 3.4 g, mp 195°–196° C. After drying at 82° C. under reduced pressure, it was submitted for elemental analysis.

Analysis: Calculated for $C_{12}H_{24}N_4O_2Cl_2$: C, 44.04; H, 7.39; N, 17.12; Found: C, 43.94; H, 7.39; N, 17.20.

EXAMPLE 49

5-Methyl-3-[[2-(1-piperidinyl)ethyl]amino]-1H-pyrazole-4-carboxylic acid ethyl ester, hydrochloride [1:2]

A stirred solution of 6 g (0.03 mole) of 4-(2-piperidinoethyl)-3-thiosemicarbazide in 30 mL of 2N ethanolic hydrogen chloride was diluted to 60 mL with absolute ethanol, treated with 4.9 g (0.03 mole) of ethyl 2-chloroacetoacetate, stirred at ambient temperature for 3 hr, and heated at reflux for 2 hr. The reaction mixture was filtered hot to remove amorphous sulfur and the filtrate concentrated to an orange oil. Trituration with refluxing 2-propyl ether and cooling gave a plastic mass with crystals. The 2-propyl ether was decanted and the residual material recrystallized from 2-propyl alcohol/2-propyl ether to give 8 g of crude product. A second recrystallization from 2-propyl alcohol/2-propyl ether gave 5.3 of beige crystalline product, mp 198°–200° C. as the dihydrochloride salt.

Analysis: Calculated for $C_{14}H_{26}N_4O_2Cl_2$: C, 47.60; H, 7.42; N, 15.86; Found: C, 47.49; H, 7.48; N, 15.88.

EXAMPLE 50

5-Methyl-3-[(1-methylethyl)amino]-1H-pyrazole-4-carboxylic acid, ethyl ester, hydrochloride [1:1]

A stirred slurry of 10.5 g (0.079 mole) of 4-(2-propanyl)-3-thiosemicarbazide in 100 mL of tetrahydrofuran under nitrogen atmosphere was treated with 13 g (0.079 mole) of ethyl 2-chloroacetoacetate. After 30 minutes the reaction mixture became suddenly exothermic, turning green-yellow and amorphous sulfur separated. The reaction mixture was stirred at ambient temperature for 2 hr, diluted with water, made acidic with 3N hydrochloric acid and filtered to remove the insoluble sulfur. The filtrate was adjusted to pH 8 with sodium carbonate and extracted with 3×50 mL of methylene chloride. The extracts were combined, washed with water, dried over magnesium sulfate and the filtrate concentrated in vacuo. The oily residue in acetone was treated with ethereal hydrogen chloride and diluted with an equal volume of isopropyl ether to give the crude product. Recrystallization from acetone gave 6.6 g of large beige crystals, mp 158°–159° C., as the hydrochloride salt.

Analysis: Calculated for $C_{10}H_{18}N_3O_2Cl$: C, 48.49; H, 7.32; N, 16.96; Found: C, 48.57; H, 7.34; N, 17.13.

EXAMPLE 51

5-Methyl-3-[[2-(4-morpholinyl)ethyl]amino]-1H-pyrazole-4-carboxylic acid, ethyl ester A stirred solution of 10 g (0.049 mole) of 4-[2-(4-morpholino)ethyl]-3-thiosemicarbazide in 50 mL of absolute ethanol under nitrogen was treated with 25 mL of 2N ethanolic hydrogen chloride and 8.1 g (0.05 mole) of ethyl 2-chloroacetoacetate, stirred at ambient temperature for 2 hr and heated at reflux for 3 hr. The reaction was filtered hot to remove amorphous sulfur and concentrated to an orange oil, 23 g. Trituration of the residue with refluxing acetone gave upon cooling a three-phase mixture consisting of solid, oil, and acetone. The solid material could not be separated from the oil. All the reaction mixture material was stirred in methanol/water and filtered through Celite ® to remove sulfur. The filtrate was extractedc with 100 mL of benzene, and adjusted to pH 8 with sodium carbonate, extracted with 2×100 mL of 2-propyl ether (no product) and extracted with 4×100 mL of methylene chloride. The methylene chloride extracts were combined, dried over magnesium sulfate and concentrated in vacuo to give a paste-like solid. Trituration of the residue with 2-propyl ether gave a yellow powder, 4.2 g, mp 124°-125° C. Recrystallization from 2-propyl ether gave 3.9 g of yellow powder, mp 124°-125° C.

Analysis: Calculated for $C_{13}H_{22}N_4O_3$: C, 55.30; H, 7.85; N, 19.84; Found: C, 55.48; H, 7.93; N, 19.58.

EXAMPLE 52

5-Methyl-3-(4-phenyl-1-piperazinyl)-1H-pyrazole-4-carboxylic acid, ethyl ester

A solution of 9 g (0.038 mole) of 4-(4-phenyl-1-piperazine)carbothioic acid hydrazide in 50 mL of 2N ethanolic hydrogen chloride was treated while stirring under nitrogen atmosphere with 6.3 g (0.038 mole) of ethyl 2-chloroacetoacetate. After stirring for 2 hr at room temperature the reaction mixture slurry was heated at reflux until it became clear (~4 hr). The reaction mixture was allowed to stir for ~16 hr without heating. The resulting solid product was dissolved by adding an additional 50 mL of absolute ethanol and heating to reflux. The hot solution was filtered to remove amorphous sulfur and upon cooling the product crystallized from the first filtrate. Filtration gave 9.3 g of a pale beige powder, mp 164°-169° C. All the product was dissolved in warm water and converted to the free base by the addition of 3N sodium hydroxide to pH 10. The oil which separated crystallized slowly and after isolation by filtration it was recrystallized from ethanol/water to give 3.7 g of silver plate-like crystals, mp 137°-138° C.

Analysis: Calculated for $C_{17}H_{22}N_4O_2$: C, 64.95; H, 7.05; N, 17.82; Found: C, 64.97; H, 7.07; N, 17.82.

EXAMPLE 53

5-Methyl-3-[3-(4-morpholino)propylamino]-1H-pyrazole-4-carboxylic acid ethylester, oxalate [1:2]

A solution of 10 g (0.46 mole) of 4-[3-(4-morpholino)propyl]-3-thiosemicarbazide in 150 mL of tetrahydrofuran was treated with 4.1 mL (0.05 mole) of concentrated hydrochloric acid. The curd-like material was stirred while 7.6 g (0.046 mole) of ethyl 2-chloroacetoacetate was added. The reaction mixture was stirred for 18 hr at room temperature, then heated at reflux for 3 hr. Upon cooling, the solid was removed by filtration dissolved in water, and the insoluble sulfur removed by filtration. The filtrate was made basic with sodium carbonate and extracted with 3×25 mL of methylene chloride which upon drying and concentrating gave 5.8 g of orange oil. The basic aqueous phase was saturated with salt, but further extractions with methylene chloride gave no additional material. After the water had evaporated from the brine solution the resulting solids were triturated with 5×100 mL of boiling isopropyl alcohol. The alcohol portions were combined and concentrated to an orange oil. TLC indicated that a majority of the residues were the starting thiosemicarbazide. All the residual oils were combined, dissolved in 150 mL of 2N ethanolic hydrogen chloride, and then treated with 7.6 g (0.046 mmol) of ethyl 2-chloroacetoacetate. The reaction mixture was heated at reflux for 2 hr and the amorphous sulfur formed was removed by filtration. The filtrate was concentrated on a rotary evaporator to give an orange semi-solid residue. This material was dissolved in hot isopropyl alcohol and upon cooling 7 g of fine yellow powder was collected by filtration. The next day the yellow powder had changed to an orange oil (hydroscopic). This oil was dissolved in 100 mL of isopropyl alcohol and washed with 50% sodium hydroxide (25 mL). The 2-propyl alcohol solution was treated with oxalic acid and after heating to dissolve the solid material, filtration and cooling gave in 2 crops a total of 4.4 g of pale yellow granular product, mp, plastic 141°-143° C., and degasses at 155°-157° C.

Analysis: Calculated for $C_{18}H_{28}N_4O_{10}$: C, 45.38; H, 5.92; N, 11.76; Found: C, 45.23; H, 5.91; N, 11.59.

EXAMPLE 54

5-Methyl-3-[4-(phenylmethyl)-1-piperazinyl]-1H-pyrazole-4-carboxylic acid, ethyl ester A stirred solution of 89 g (0.36mole) of 4-(methylphenyl)piperazinecarbothoic acid hydrazide in 500 mL of 2N ethanolic hydrogen chloride under nitrogen atmosphere was treated with 58.5 g (0.36 mole) of ethyl 2-chloroacetoacetate. The reaction mixture turned yellow quickly and was stirred at ambient temperature for 4 hr, heated at reflux for 1 hr and stirred for ~16 hr at ambient temperature. The yellow-white precipitate could not be dissolved in the reaction mixture solvent by heating, or after adding 700 mL of additional ethanol and heating to reflux. The reaction mixture was cooled and the solid removed by filtration, yielding 158.8 g of mostly white product tinged with yellow sulfur. A sample was recrystallized 3 times from ethanol, mp 218°-222° C. (degasses). A 12 g portion was recovered from a second reaction mixture as the crystalline free base and recrystallization of this material from 2-propyl ether/ligroin with aid of a soxhlet extraction gave 8.3 g of white crystalline product, mp 124°-126° C.

Analysis: Calculated for $C_{18}H_{24}N_4O_2$: C, 65.83; H, 7.37; N, 17.06; Found: C, 65.96; H, 7.39; N, 17.13.

EXAMPLE 55

5-Methyl-3-(1-piperazinyl)-1H-pyrazole-4-carboxylic acid, ethyl ester, hydrochloride [1:2]

A slurry of 10 g (0.03 mole) of 5-methyl-3-[(4-phenylmethyl)-1-piperazinyl]-1H-pyrazole-4-carboxylic acid ethyl ester in 150 mL of ethanol was treated with 50 mL of 3N hydrochloric acid then with 1 g of 5% palladium on carbon. This mixture was hydrogenated on a Parr apparatus with 43 psi of hydrogen gas at ~60° C. After 3 hr, the reaction mixture was cooled, filtered to remove the catalyst, and the filtrate concentrated in vacuo to give a solid residue. Recrystallization from absolute ethanol yielded 6.8 g of white crystalline product, mp 254°–256° C. with degassing.

Analysis: Calculate for $C_{11}H_{20}N_4O_2Cl_2$: C, 42.45; H, 6.48; N, 18.00; Found: C, 42.46; H, 6.44; N, 17.93.

EXAMPLE 56

5-Methyl-3-[4-(trifluoromethyl)phenylamino]-1H-pyrazole-4-carboxylic acidethyl ester.

When in the procedure of Example 1 and utilizing Method A, reacting the following in sequence:
(1) 4-(4-(trifluoromethyl)phenyl-3-thiosemicarbazide, and
(2) ethyl 2-chloroacetoacetate, the title compound is obtained.

EXAMPLE 57

When in the procedure of Example 45 and substituting the following for 4-morpholine carbothioic acid hydrazide:
(a) 1-pyrrolidinecarbothioic acid hydrazide
(b) 1-piperidinecarbothioic acid hydrazide
(c) 1-homopiperidinecarbothioic acid hydrazide
there are obtained:
(a) 5-methyl-3-(1-pyrrolidinyl)-1H-pyrazole-4-carboxylic acid, ethyl ester
(b) 5-methyl-3-(1-piperidinyl)-1H-pyrazole-4-carboxylic acid, ethyl ester
(c) 3-(1-homopiperidinyl)-5-methyl-1H-pyrazole-4-carboxylic acid, ethyl ester.

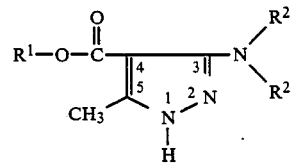

Formula I

| Example Number | $R^1$ | $-NR^2R^3$ | Salt | Melting Point |
|---|---|---|---|---|
| 1 | $C_2H_5$ | $-NHC_6H_5$ | — | 165–166° C. |
| 2 | $C_2H_5$ | $-NH[4-Cl(C_6H_4)]$ | — | 223–225° C. |
| 3 | $C_2H_5$ | $-NH[3-SCH_3(C_6H_4)]$ | — | 191.5–194° C. |
| 4 | $C_2H_5$ | (1-naphthalenyl)amino | — | 199–202° C. |
| 5 | $C_2H_5$ | $-NH[2-SCH_3(C_6H_4)]$ | — | 140.5–142° C. |
| 6 | $C_2H_5$ | $-NH[2,6-(CH_3)_2(C_6H_3)]$ | — | 142–144° C. |
| 7 | $C_2H_5$ | $-NH[2-OCH_3(C_6H_4)]$ | — | 184–192° C. |
| 8 | $C_2H_5$ | $-NH[2-CH_3(C_6H_4)]$ | — | 160–161° C. |
| 9 | $C_2H_5$ | $-NH[2,6-Cl_2(C_6H_3)]$ | — | 191–192° C. |
| 10 | $C_2H_5$ | $-NH[2-Cl_2(C_6H_4)]$ | — | 188–189° C. |
| 11 | $C_2H_5$ | $-NH[2,4-(OCH_3)_2(C_6H_3)]$ | HCl[1:1] | 199–200° C. |
| 12 | $C_2H_5$ | $-NH[3-Cl(C_6H_4)]$ | — | 159.5–160° C. |
| 13 | $C_2H_5$ | (2-pyridinyl)amino | — | 155–156° C. |
| 14 | $C_2H_5$ | $-NH[(CH_2)_3CH_3]$ | — | 109–110° C. |
| 15 | $C_2H_5$ | $-NH[(CH_2)_3CH_3]$ | sulfate[1:1] | 81–83° C. |
| 16 | $C_2H_5$ | $-NH[2,6-(C_2H_5)_2(C_6H_3)]$ | HCl[1:1] | 167–170° C. |
| 17 | $C_2H_5$ | $-NH[2,4-(CH_3)_2(C_6H_3)]$ | — | 174.5–176° C. |
| 18 | $C_2H_5$ | $-NH[2-CH_3-4-Cl(C_6H_3)]$ | — | 156–187° C. |
| 19 | $C_2H_5$ | $-NH[2,4-Cl_2(C_6H_3)]$ | — | 214–217° C. |
| 20 | $C_2H_5$ | $-NH[2-Cl,6-CH_3(C_6H_3)]$ | — | 158–159° C. |
| 21 | $C_2H_5$ | $-NH[2,6-(CH_3)_2,4-Br-(C_6H_2)]$ | — | 184–185° C. |
| 22 | $C_2H_5$ | $-NHCH_3$ | — | 161–162° C. |
| 23 | $C_2H_5$ | $-NH(-CH_2CH=CH_2)$ | HCl[1:1] | 133–134° C. |
| 24 | $C_2H_5$ | $-NH(C_2H_5)$ | HCl[1:1] | 140–148° C. |
| 25 | $C_2H_5$ | $-NH(C_6H_{11})$ | HCl[1:1] | 178–182° C. |
| 26 | $C_2H_5$ | $-NH[-CH_2(C_6H_5)]$ | — | 149–150° C. |
| 27 | $C_2H_5$ | $-NH_2$ | HCl[1:1] | 186–188° C. |
| 28 | $C_2H_5$ | (1-adamantyl)amino | — | 190–203° C. |
| 29 | $C_2H_5$ | $-N(CH_3)_2$ | HCl[1:1] | 137–139° C. |
| 30 | $C_2H_5$ | $-NH[-(CH_2)_2-C_6H_5]$ | — | 138–139° C. |
| 31 | $C_2H_5$ | $-NH[-(CH_2)_6-CH_3]$ | HCl[1:1] | 83–84° C. |
| 32 | $C_2H_5$ | $-NH[-C(CH_3)_3]$ | — | 118–119° C. |
| 33 | $C_2H_5$ | $-NH[C_7H_{13}]$ | HCl[1:1] | 155–161° C. |
| 34 | $C_2H_5$ | $-NH[C_5H_9]$ | HCl[1:1] | 175–177° C. |
| 35 | $C_2H_5$ | $-NH[C_3H_5]$ | HCl[1:1] | 151–152° C. |
| 36 | $C_2H_5$ | $-NH[-(CH_2)_2-CH_3]$ | HCl[1:1] | 155–161° C. |
| 37 | $C_2H_5$ | (1-methylpropyl)amino | HCl[1:1] | 147–149° C. |
| 38 | $C_2H_5$ | $-NH[-(CH_2)_4-CH_3]$ | — | 117–119° C. |
| 39 | $C_2H_5$ | $-NH[-(CH_2)_5CH_3]$ | HCl[1:1] | 108–109° C. |
| 40 | $C_2H_5$ | $-NH[-C_8H_{15}]$ | HCl[1:1] | 168–171° C. |
| 41 | $C_2H_5$ | (2-methylbutyl)amino | HCl[1:1] | 130–133° C. |
| 42 | $C_2H_5$ | (1,1,3,3-tetramethylbutyl)amino | HCl[1:1] | 167–168° C. |
| 43 | $C_2H_5$ | $-N[-(CH_2)_3CH_3]_2$ | HCl[1:1] | 159–162° C. |
| 44 | $C_2H_5$ | 4-morpholinyl | HCl[1:1] | 165–173° C. |
| 45 | H | $-NH(C_6H_{11})$ | — | 162–163° C. |
| 46 | $C_2H_5$ | $-N(CH_3)(C_6H_{11})$ | HCl[1:1] | 156–158° C. |
| 47 | $C_2H_5$ | $-N(CH_3)(C_5H_9)$ | HCl[1:1] | 144–146° C. |
| 48 | $C_2H_5$ | $-NH[-(CH_2)_3-N(CH_3)_2]$ | HCl[1:2] | 195–196° C. |
| 49 | $C_2H_5$ | 2-(1-piperidinyl)ehtyl]amino | HCl[1:2] | 198–200° C. |
| 50 | $C_2H_5$ | $-NH[CH(CH_3)_2]$ | HCl[1:1] | 158–159° C. |
| 51 | $C_2H_5$ | [2-(4-morpholinyl)ethyl]amino | — | 124–125° C. |

-continued

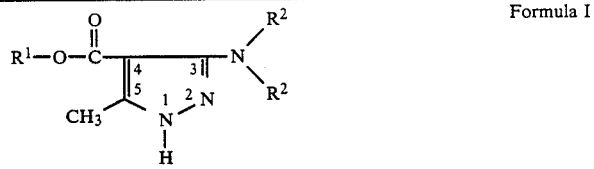

Formula I

| Example Number | R¹ | —NR²R³ | Salt | Melting Point |
| --- | --- | --- | --- | --- |
| 52 | $C_2H_5$ | 4-phenyl-1-piperazinyl | — | 137–138° C. |
| 53 | $C_2H_5$ | [3-(4-morpholino)propyl]amino | oxalate[1:2] | 155–157° C. |
| 54 | $C_2H_5$ | 4-(phenylmethyl)-1-piperazinyl | — | 124–126° C. |
| 55 | $C_2H_5$ | 1-piperazinyl | HCl[1:2] | 254–256° C. |
| 56 | $C_2H_5$ | $-NH[4-CF_3-(C_6H_4)]$ | — | — |
| 57a | $C_2H_5$ | 1-pyrrolidinyl | — | — |
| 57b | $C_2H_5$ | 1-piperidinyl | — | — |
| 57c | $C_2H_5$ | 1-homopiperidinyl | — | — |

PHARMACOLOGICAL TEST PROCEDURES
MUSCLE RELAXANT TEST

The test procedure used to indicate positive muscle relaxant activity is the Morphine-Induced Straub Tail Test described by G. D. Novak in Drug Development Research (1982) 2: 383–386, except 8 animals per group were used rather than 10 per test. The test is summarized as follows: the test drug, reference drug, and control articles to be administered are prepared in saline, 0.5% aqueous methylcellulose suspension, or other solvent depending on solubility, in such concentration that the volume administered is 10 mL/kg. The initial screening dose of the test drug is usually 100 mg/kg. Groups of 8 mice are given an intraperitoneal dose of a compound or vehicle prepared as described above. After 15 min, mice are administered morphine sulfate, 60 mg/kg, subcutaneously. Fifteen minutes after administration of morphine (i.e., 30 min after test compound administration), mice were scored for presence of Straub Tail, defined as an elevation of the tail at least 90 degrees from the horizontal. An $ED_{50}$ value may be determined from at least three logarithmically spaced doses, using the method of Litchfield and Wilcoxon (1949), J. Pharmacol. Exp. Ther. 96: 99–113. Illustratively, some of more active compounds such as those prepared in Examples 39 and 43 exhibited $ED_{50}$ values of 15–50 mg/kg in the foregoing Straub Tail Test.

Anticonvulsant activity was determined for compounds of Formula I as evidenced by using chemical or electrical challenge as follows:

Metrazole Chemical Challenge (Swinyard Method)

Groups of 8 adults female mice were randomly assigned to dosage groups according to the method of Steel, R. G. C., and Torrie, J. H. (1960) in "Principles and Procedures of Statistics," McGraw-Hill Book Company, Inc., pp 99–100, pp 428–31. Each mouse was identified with a color code on its tail. The test compounds were administered as solutions or suspensions in 10 mL/kg mouse body weight of 0.5% aqueous methylcellulose suspension within 15 minutes of preparation of the suspension. Metrazole ® (pentylenetetrazol) was prepared as a solution in physiological saline. The mice were not fasted prior to the test. Eight mice were tested at each dosage level.

Each mouse received one dose of the test drug (usually 100 mg/kg for screening) in 0.5% aqueous methylcellulose or the control article (0.5% aqueous methylcellulose alone) intraperitoneally. Metrazole (80 mg/kg S.C.) was then given in a loose fold of skin on the back of the neck 0.5 hr after the test compound or control article was given.. Injections were given with a 1 mL glass tuberculin syringe with appropriate size hypodermic needle (27 gauge for solutions; 23 gauge for suspensions). All injections were given in a volume of 10 mL/kg mouse body weight. Each mouse was observed for 30 minutes following Metrazol injection. Failure of the animals to exhibit a threshold seizure (a single episode of clonic spasms at least 5 seconds in duration) was defined as protection. Anticonvulsant data were tabulated as the percent protection, i.e., (No. Mice Protected/No. Mice Tested)×100.

The $ED_{50}$, 95% confidence limits and potency ratio may be ascertained by the computer-based probit analysis ascribed to Finney, D. J., Statistical Method in Biological Assay, 2nd Ed., Hefner Publishing Co., New York (1964). Illustratively, some of the more active compounds such as those of Examples 14, 25, 33, 40, and 42 exhibit $Ed_{50}$ values of 20–50 mg/kg in the foregoing metrazole test.

Electrical Challenge

Adult female mice in groups of eight were administered the test drug intraperitoneally (usually 100 mg/kg initially for screening) in liquid carrier, usually physiological saline, water or 0.5% aqueous methylcellulose suspension as described above. Animals were challenged electrically by placing brass electrodes on the corneas and applying an electrical stimulus (60 Hz, 5 m sec. pulse width, 34 mA intensity) for 0.2 seconds by way of a Grass Stimulator ® and constant current unit and a Hunter Timer ®. The absence of tonic seizures upon cessation of the stimuli was scored as protection in that animal. The number of animals protected from tonic seizures at a given dose of test drug was determined. The $ED_{50}$, 95% confidence limits and potency ratio may be ascertained by the method of J. T. Litchfield and F. Wilcoxon (1949) J. Pharmacol. Exp. Ther. 96, 99–113. Illustratively, some of the more active compounds such as those of Examples 15, 25, 33, 34, 35, 36, 37, 40, 42, 44, 47, and 50 exhibit $ED_{50}$ values in the range of 10–50 mg/kg.

Antianxiety Test

The test screening procedure used on to indicate positive antianxiety response is a modification of the Vogel Conflict Test which is based on shock-suppressed drinking behavior in rats outlined by J. R. Vogel, et al., in Psychopharmacology 21: 1–7 (1971). The procedure used is as follows: the test, reference, and control articles are administered intraperitoneally in physiological saline, 0.5% aqueous methylcellulose, or other solvent depending on a solubility in such concentration that the volume administered is 5 mg/kg. The initial screening dose of the test article is usually 100.0 mg/kg.

Prior to dosing, rats are housed 2 per cage and deprived of water for 48 hr and thereafter randomized into treatment groups of five. Feed is available ad libitum. Thirty minutes after dosing, each rat is placed individually in a plexiglass cage measuirng 18 cm in width, 13 cm in height, and 29.5 cm in length and equipped with a stainless-steel grid floor. The cage is covered with a plastic lid containing holes to facilitate introduction of a water bottle (30 mL plastic centrifuge tube) with a rubber stopper and metal drinking tube. A Drinkometer circuit (Omniteck Electronics, Inc., 3000 Cortona Road, Columbus, Ohio 43204) is connected between the drinking tube and the grid floor of the apparatus so that the rat completes the circuit whenever it licks the tube. The procedure is to allow the rat to find the drinking tube and complete 20 licks (as displayed on the Drinkometer digital readout) prior to the start of the experimental session. Rats not reaching this criterion are discarded. A three minute experimental session is initiated by a 0.25 mA shock at the 20th lick. Rats that continue drinking will experience a shock at each successive 20th lick. The total number of shocks during the experimental session are recorded as follows:

(total licks/20)+1=total shocks

Statistical analysis is performed by the Dunn's Multiple Comparison Test described by O. J. Dunn, Technometrics, 6(3): 241–52 (1964). The mean number of shocks experienced by the control group is compared with those of each drug-treated group. Significance is considered at $P<0.1$. The higher the total shocks compared to control, the more active is the compound. Active compounds may then be similarly tested at reduced dosages. Five rats were tested at a given dosage level and 5 rats were used as controls. Illustratively, some of the more active compounds such as those of Examples 14, 33 and 35 exhibited MED (Minimum Effective Dose) values of 3–100 mg/kg in the foregoing Vogel Conflict Test.

Pharmaceutical Compositions

The methods of treating anxiety, muscle tension, and spasticity in mammals are best carried out by administering as active ingredients in a pharmaceutical composition at least one of the compounds of Formula I in association with a pharmaceutically acceptable carrier or excipient. The compounds are thus presented in a therapeutic composition suitable for oral, rectal, parenteral, subcutaneous, intramuscular, intraperitoneal, or intravenous administration. Thus, for example, the composition for oral administration can take the form of elixirs, capsules, tablets, or coated tablets containing carriers or excipients conveniently used in the pharmaceutical art. Suitable tableting excipients include lactose, potato, and maize starches, talc, gelatin, stearic and silicic acids, magnesium stearate and polyvinyl pyrrolidone.

For parenteral administration the carrier can be comprised of a sterile parenterally acceptable liquid; e.g., water or arachis oil contained in ampoules.

In compositions for rectal administration, the carrier or excipient can be comprised of a suppository base; e.g., cocoa butter or glyceride.

Advantageously, the compositions are formulated as dosage units, each unit being adapted to supply a fixed dose of active ingredient. Tablets, coated tablets, capsules, ampoules and suppositories are examples of preferred dosage forms according to the invention. It is only necessary that the active ingredient constitute an effective amount; i.e., such that a suitable effective dosage will be consistent with the dosage form employed. The exact individual dosages as well as daily dosages will, of course, be determined according to standard medical principles under the direction of a physician or veterinarian.

Animal testing suggests that the more active compounds of Formula I such as those cited above in the Vogel test will be effective in humans for relief from anxiety at 3 to 100 mg/kg body weight per day. Thus an active compound such as Example 14 may be administered to control anxiety in unit dosage form to an adult human at 70–1,000 mg once, twice or three times a day.

Animal testing suggests that the more active compounds of Formula I will be effective in humans for muscle relaxant effects at 15 to 100 mg/kg body weight per day. Thus, an active compound such as that of Example 33 may be administered to effectively control muscle spasms in unit dosage form to an adult human at 300–1,000 mg once, twice or three times a day.

The compounds of Formula I have anticonvulsant property as exhibited by activity against seizures caused by electrical or chemical challenge. The animal data suggest the more active compounds of Formula I, such as those cited above under Electroshock Experiments and metrazole chemical challenge are projected to be effective against all types of epilepsy. The animal data suggest the more active compounds of Formula I will be effective in humans at 5–15 mg/kg body weight per day. Thus an active compound such as that of Example 42 may be administered to effectively control all types of epilepsy, both grand mal and petit mal, seizures. For example, oral daily doses of 100–1,000 mg of active agent once, twice or three times a day are projected for treatment of epilepsy.

The active ingredients of the invention may be combined with other pharmacologically active agents as previously indicated, or with buffers, antacids or the like, for administration and the proportion of the active agent in the composition may be varied widely.

Capsules

Capsules of 5 mg, 25 mg, and 50 mg of active ingredient per capsule are prepared; with higher amounts of ingredient reduction may be made in the amount of lactose.

| Typical Blend for Encapsulation | Per Capsule (mg) |
|---|---|
| Active Ingredient | 5.0 |
| Lactose | 296.7 |
| Starch | 129.0 |
| Magnesium Stearate | 4.3 |
| Total | 435.0 |

Uniformly blend the selected active ingredient with lactose, starch, and magnesium stearate and encapsulate the blend.

Additional capsule formulations preferably contain a higher dose of active ingredient and are as follows:

| Ingredients | 100 mg per Capsule | 250 mg per Capsule | 500 mg per Capsule |
|---|---|---|---|
| Active Ingredient | 100.0 | 250.0 | 500.0 |
| Lactose | 231.5 | 126.5 | 31.1 |
| Starch | 99.2 | 54.2 | 13.4 |
| Magnesium Stearate | 4.3 | 4.3 | 5.5 |
| Total (mg) | 435.0 | 435.0 | 550.0 |

Uniformly blend the selected active ingredient with Lactose, Starch and Magnesium Stearate and encapsulate the blend.

Tablets

A typical formulation for a tablet containing 5.0 mg to 50.0 mg of active ingredient per tablet follows. The formulation may be used for other strengths of active ingredient by adjustment of weight of dicalcium phosphate and active ingredient.

| Ingredients | Per Tablet (5 mg) | Per Tablet (50 mg) |
|---|---|---|
| (1) Active Ingredient | 5.0 | 50.0 |
| (2) Corn Starch | 13.6 | 13.6 |
| (3) Corn Starch (paste) | 3.4 | 3.4 |
| (4) Lactose | 79.2 | 79.2 |
| (5) Dicalcium Phosphate | 68.0 | 23.0 |
| (6) Calcium Stearate | 0.9 | 0.9 |
| Total | 170.1 | 170.1 |

Uniformly blend 1, 2, 4, and 5. Prepare 3 as a 10 percent paste in water. Granulate the blend with the starch paste and pass the wet mass through a number eight mesh screen. The wet granulation is dried and passed through a number twelve mesh screen. The dried granules are blended with calcium stearate and compressed.

Additional tablet formulations preferably contain a higher dosage of the active ingredient and are as follows:

| Ingredients | 100 mg per Tablet | 250 mg per Tablet | 500 mg per Tablet |
|---|---|---|---|
| Active Ingredient | 100.0 | 250.0 | 500.0 |
| Lactose | 180.0 | 150.0 | 200.0 |
| Corn Starch | 116.0 | 100.0 | 100.0 |
| Calcium Stearate | 4.0 | 5.0 | 8.0 |
| Total (mg) | 400.0 | 505.0 | 808.0 |

Uniformly blend the active ingredient, lactose, and corn starch. The blend is granulated, using water as a granulating medium. The wet granules are passed through an eight mesh screen and dried at 140 to 160 degrees Fahrenheit overnight. The dried granules are passed through a number ten mesh screen and blended with the proper amount of calcium stearate and this blend is then converted into tablets on a suitable tablet press.

Various modifications and equivalents will be apparent to one skilled in the art and may be made in the compounds, methods, processes and pharmaceutical compositions of the present invention without departing from the spirit and scope thereof; and it is therefore to be understood that the invention is to be limited only by the scope of the appended claims.

What is claimed is:

1. A method of treating convulsions, muscle tension and anxiety in mammals which comprises administering to mammals in need of such treatment an effective amount for treating convulsions, muscle tension and anxiety of a compound having the formula:

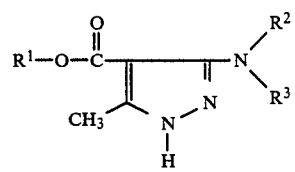

wherein $R^1$ is hydrogen, loweralkyl or a pharmaceutically acceptable cation;

$R^2$ and $R^3$, same or different, are hydrogen, loweralkyl, aryl, cycloalkyl, loweralkenyl, 1-adamantyl, heterocyclicaminoalkyl, or diloweralkylaminoloweralkyl;

and the pharmaceutically acceptable salts or tautomeric isomers thereof.

2. The method of claim 1 wherein the compound administered is 5-methyl-3-phenylamino-1H-pyrazole-4-carboxylic acid ethyl ester or a pharmaceutically accpetable salt thereof.

3. The method of claim 1 wherein the compound administered is 3-[4-(chlorophenyl)amino]-5-methyl-1H-pyrazole-4-carboxylic acid ethyl ester or a pharmaceutically acceptable salt thereof.

4. The method of claim 1 wherein the compound administered is 5-methyl-3-[[3-(methylthio)phenyl]amino]-1H-pyrazole-4-carboxylic acid ethyl ester or a pharmaceutically acceptable salt thereof.

5. The method of claim 1 wherein the compound administered is 5-methyl-3-(1-naphthalenylamino)-1H-pyrazole-4-carboxylic acid ethyl ester or a pharmaceutically acceptable salt thereof.

6. The method of claim 1 wherein the compound administered is 5-methyl-3-[[2-(methylthio)phenyl]amino]-1H-pyrazole-4-carboxylic acid ethyl ester or a pharmaceutically acceptable salt thereof.

7. The method of claim 1 wherein the compound administered is 5-methyl-3-[2,6-dimethylphenyl)amino]-1H-pyrazole-4-carboxylic acid ethyl ester or a pharmaceutically acceptable salt thereof.

8. The method of claim 1 wherein the compound administered is 5-methyl-3-[(2-methoxyphenyl)amino]-1H-pyrazole-4-carboxylic acid ethyl ester or a pharmaceutically acceptable salt thereof.

9. The method of claim 1 wherein the compound administered is 5-methyl-3-[(2-methylphenyl)amino]-1H-pyrazole-4-carboxylic acid ethyl ester or a pharmaceutically acceptable salt thereof.

10. The method of claim 1 wherein the compound administered is 3-[(2,6-dichlorophenyl)amino]-5-methyl-1H-pyrazole-4-carboxylic acid ethyl ester or a pharmaceutically acceptable salt thereof.

11. The method of claim 1 wherein the compound administered is 3-[(2-chlorophenyl)amino]-5-methyl-1H-pyrazole-4-carboxylic acid ethyl ester or a pharmaceutically acceptable salt thereof.

12. The method of claim 1 wherein the compound administered is 3-[(2,4-dimethoxyphenyl)amino]-5- methyl-1H-pyrazole-4-carboxylic acid ethyl ester or a pharmaceutically acceptable salt thereof.

13. The method of claim 1 wherein the compound administered is 3-[(3-chlorophenyl)amino]-5-methyl-1H-pyrazole-4-carboxylic acid ethyl ester or a pharmaceutically acceptable salt thereof.

14. The method of claim 1 wherein the compound administered is 3-butylamino-5-methyl-1H-pyrazole-4-carboxylic acid ethyl ester or a pharmaceutically acceptable salt thereof.

15. The method of claim 1 wherein the compound administered is 3-[(2,6-diethylphenyl)amino]-5-methyl-1H-pyrazole-4-carboxylic acid ethyl ester or a pharmaceutically acceptable salt thereof.

16. The method of claim 1 wherein the compound administered is 3-[(2,4-dimethylphenyl)amino]-5-methyl-1H-pyrazole-4-carboxylic acid ethyl ester or a pharmaceutically acceptable salt thereof.

17. The method of claim 1 wherein the compound administered is 3-[(4-chloro-2-methylphenyl)amino]-5-methyl-1H-pyrazole-4-carboxylic acid ethyl ester or a pharmaceutically acceptable salt thereof.

18. The method of claim 1 wherein the compound administered is 3-[(2,4-dichlorophenyl)amino]-5-methyl-1H-pyrazole-4-carboxylic acid ethyl ester or a pharmaceutically acceptable salt thereof.

19. The method of claim 1 wherein the compound administered is 3-[(2-chloro-6-methylphenyl)amino]-5-methyl-1H-pyrazole-4-carboxylic acid ethyl ester or a pharmaceutically acceptable salt thereof.

20. The method of claim 1 wherein the compound administered is 3-[(4-bromo-2,6-dimethylphenyl)amino]-5-methyl-1H-pyrazole-4-carboxylic acid ethyl ester or a pharmaceutically acceptable salt thereof.

21. The method of claim 1 wherein the compound administered is 5-methyl-3-(methylamino)-1H-pyrazole-4-carboxylic acid ethyl ester or a pharmaceutically acceptable salt thereof.

22. The method of claim 1 wherein the compound administered is 5-methyl-3-[(2-propenyl)amino]-1H-pyrazole-4-carboxylic acid ethyl ester or a pharmaceutically acceptable salt thereof.

23. The method of claim 1 wherein the compound administered is 3-ethylamino-5-methyl-1H-pyrazole-4-carboxylic acid ethyl ester or a pharmaceutically acceptable salt thereof.

24. The method of claim 1 wherein the compound administered is 3-(cyclohexylamino)-5-methyl-1H-pyrazole-4-carboxylic acid ethyl ester or a pharmaceutically acceptable salt thereof.

25. The method of claim 1 wherein the compound administered is 5-methyl-3-[(phenylmethyl)amino]-1H-pyrazole-4-carboxylic acid ethyl ester or a pharmaceutically acceptable salt thereof.

26. The method of claim 1 wherein the compound administered is 3-amino-5-methyl-1H-pyrazole-4-carboxylic acid ethyl ester or a pharmaceutically acceptable salt thereof.

27. The method of claim 1 wherein the compound administered is 3-(1-adamantyl)-5-methyl-1H-pyrazole-4-carboxylic acid ethyl ester or a pharmaceutically acceptable salt thereof.

28. The method of claim 1 wherein the compound administered is 3-(dimethylamino)-5-methyl-1H-pyrazole-4-carboxylic acid ethyl ester or a pharmaceutically acceptable salt thereof.

29. The method of claim 1 wherein the compound administered is 5-methyl-3-[(2-phenylethyl)amino]-1H-pyrazole-4-carboxylic acid ethyl ester or a pharmaceutically acceptable salt thereof.

30. The method of claim 1 wherein the compound administered is 3-(heptylamino)-5-methyl-1H-pyrazole-4-carboxylic acid ethyl ester or a pharmaceutically acceptable salt thereof.

31. The method of claim 1 wherein the compound administered is 3-[(1,1-dimethylethyl)amino]-5-methyl-1H-pyrazole-4-carboxylic acid ethyl ester or a pharmaceutically acceptable salt thereof.

32. The method of claim 1 wherein the compound administered is 3-[(cycloheptyl)amino]-5-methyl-1H-pyrazole-4-carboxylic acid ethyl ester or a pharmaceutically acceptable salt thereof.

33. The method of claim 1 wherein the compound administered is 3-[(cyclopentyl)amino]-5-methyl-1H-pyrazole-4-carboxylic acid ethyl ester or a pharmaceutically acceptable salt thereof.

34. The method of claim 1 wherein the compound administered is 3-[(cyclopropyl)amino]-5-methyl-1H-pyrazole-4-carboxylic acid ethyl ester or a pharmaceutically acceptable salt thereof.

35. The method of claim 1 wherein the compound administered is 5-methyl-3-(propylamino)-1H-pyrazole-4-carboxylic acid ethyl ester or a pharmaceutically acceptable salt thereof.

36. The method of claim 1 wherein the compound administered is 5-methyl-3-[(1-methylpropyl)amino]-1H-pyrazole-4-carboxylic acid ethyl ester or a pharmaceutically acceptable salt thereof.

37. The method of claim 1 wherein the compound administered is 5-methyl-3-(pentylamino)-1H-pyrazole-4-carboxylic acid ethyl ester or a pharmaceutically acceptable salt thereof.

38. The method of claim 1 wherein the compound administered is 3-(hexylamino)-5-methyl-1H-pyrazole-4-carboxylic acid ethyl ester or a pharmaceutically acceptable salt thereof.

39. The method of claim 1 wherein the compound administered is 3-[(cyclooctyl)amino]-5-methyl-1H-pyrazole-4-carboxylic acid ethyl ester or a pharmaceutically acceptable salt thereof.

40. The method of claim 1 wherein the compound administered is 5-methyl-3-[(2-methylbutyl)amino]-1H-pyrazole-4-carboxylic acid ethyl ester or a pharmaceutically acceptable salt thereof.

41. The method of claim 1 wherein the compound administered is 5-methyl-3-[(1,1,3,3-tetramethylbutyl)amino]-1H-pyrazole-4-carboxylic acid ethyl ester or a pharmaceutically acceptable salt thereof.

42. The method of claim 1 wherein the compound administered is 3-(dibutylamino)-5-methyl-1H-pyrazole-4-carboxylic acid ethyl ester or a pharmaceutically acceptable salt thereof.

43. The method of claim 1 wherein the compound administered is 3-[(cyclohexyl)amino]-5-methyl-1H-pyrazole-4-carboxylic acid or a pharmaceutically acceptable salt thereof.

44. The method of claim 1 wherein the compound administered is 3-[(cyclohexyl)(methyl)amino]-5-methyl-1H-pyrazole-4-carboxylic acid ethyl ester or a pharmaceutically acceptable salt thereof.

45. The method of claim 1 wherein the compound administered is 3-[(cyclopentyl)(methyl)amino]-5-methyl-1H-pyrazole-4-carboxylic acid ethyl ester or a pharmaceutically acceptable salt thereof.

46. The method of claim 1 wherein the compound administered is 3-[[3-(dimethylamino)-1-propyl]amino]-

5-methyl-1H-pyrazole-4-carboxylic acid ethyl ester or a pharmaceutically acceptable salt thereof.

47. The method of claim 1 wherein the compound administered is 5-methyl-3-[(1-methylethyl)amino]-1H-pyrazole-4-carboxylic acid ethyl ester or a pharmaceutically acceptable salt thereof.

48. A method of treating muscle tension in mammals which comprises administering to mammals in need of such treatment an effective amount for treating muscle tension of a compound having the formula:

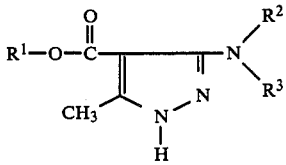

wherein,
R¹ is hydrogn, loweralkyl or a pharmaceutically acceptable cation;
R² and R³, same or different, are hydrogen, loweralkyl, aryl, cycloalkyl, loweralkenyl, 1-adamantyl, heterocyclicaminoalkyl, or diloweralkylaminoloweralkyl; and the pharmaceutically acceptable salts or tautomeric isomers thereof.

49. The method of claim 48 wherein the compound administered is 3-(hexyl-amino)-5-methyl-1H-pyrazole-4-carboxylic acid ethyl ester or a pharmaceutically acceptable salt thereof.

50. The method of claim 48 wherein the compound administered is 3-(dibutylamino)-5-methyl-1H-pyrazole-4-carboxylic acid ethyl ester or a pharmaceutically acceptable salt thereof.

51. A method of treating convulsions in mammals which comprises administering to mammals in need of such treatment an effective amount for treating convulsions of a compound having the formula:

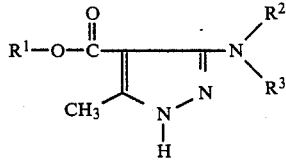

wherein,
R¹ is hydrogen, loweralkyl or a pharmaceutically acceptable cation;
R² and R³, same or different, are hydrogen, loweralkyl, aryl, cycloalkyl, loweralkenyl, 1-adamantyl, heterocyclicaminoalkyl, or diloweralkylaminoloweralkyl; and the pharmaceutically acceptable salts or tautomeric isomers thereof.

52. The method of claim 51, wherein the compound administered is 3-butylamino-5-methyl-1H-pyrazole-4-carboxylic acid ethyl ester or a pharmaceutically acceptable salt thereof.

53. The method of claim 51, wherein the compound administered is 3-[(cyclohexyl)amino]-5-methyl-1H-pyrazole-4-carboxylic acid ethyl ester or a pharmaceutically acceptable salt thereof.

54. The method of claim 51 wherein the compound administered is 3-[(cycloheptyl)amino]-5-methyl-1H-pyrazole-4-carboxylic acid ethyl ester or a pharmaceutically acceptable salt thereof.

55. The method of claim 51 wherein the compound administered is 3-[(cyclopentyl)amino]-5-methyl-1H-pyrazole-4-carboxylic acid ethyl ester or a pharmaceutically acceptable salt thereof.

56. The method of claim 51 wherein the compound administered is 3-[(cyclopropyl)amino]-5-methyl-1H-pyrazole-4-carboxylic acid ethyl ester or a pharmaceutically acceptable salt thereof.

57. The method of claim 51 wherein the compound administered is 5-methyl-3-(propylamino)-1H-pyrazole-4-carboxylic acid ethyl ester or a pharmaceutically acceptable salt thereof.

58. The method of claim 51 wherein the compound administered is 5-methyl-3-[(1-methylpropyl)amino]-1H-pyrazole-4-carboxylic acid ethyl ester or a pharmaceutically acceptable salt thereof.

59. The method of claim 51 wherein the compound administered is 3-[(cyclooctyl)amino]-5-methyl-1H-pyrazole-4-carboxylic acid ethyl ester or a pharmaceutically acceptable salt thereof.

60. The method of claim 51 wherein the compound administered is 5-methyl-3-[(1,1,3,3-tetramethylbutyl)amino]-1H-pyrazole-4-carboxylic acid ethyl ester or a pharmaceutically acceptable salt thereof.

61. The method of claim 51 wherein the compound administered is 3-[(cyclopentyl)(methyl)amino]-5-methyl-1H-pyrazole-4-carboxylic acid ethyl ester or a pharmaceutically acceptable salt thereof.

62. The method of claim 51 wherein the compound administered is 5-methyl-3-[(1-methylethyl)amino]-1H-pyrazole-4-carboxylic acid ethyl ester or a pharmaceutically acceptable salt thereof.

63. A method of treating anxiety in mammals which comprises administering to mammals in need of such treatment an effective amount for treating anxiety of a compound having the formula:

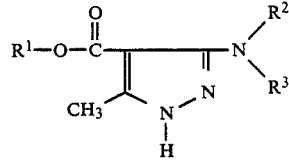

wherein,
R¹ is hydrogen, loweralkyl or a pharmaceutically acceptable cation;
R² and R³, same or different, are hydrogen, loweralkyl, aryl, cycloalkyl, loweralkenyl, 1-adamantyl, heterocyclicaminoalkyl, or diloweralkylaminoloweralkyl; and the pharmaceutically acceptable salts or tautomeric isomers thereof.

64. The method of claim 63, wherein the compound administered is 3-butylamino-5-methyl-1H-pyrazole-4-carboxylic acid ethyl ester or a pharmaceutically acceptable salt thereof.

65. The method of claim 63, wherein the compound administered is 3-[(cycloheptyl)amino]-5-methyl-1H-pyrazole-4-carboxylic acid ethyl ester or a pharmaceutically acceptable salt thereof.

66. The method of claim 63, wherein the compound administered is 3-[(cyclopropyl)amino]-5-methyl-1H-pyrazole-4-carboxylic acid ethyl ester or a pharmaceutically acceptable salt thereof.

* * * * *